US008304553B2

(12) United States Patent
Liu et al.

(10) Patent No.: US 8,304,553 B2
(45) Date of Patent: Nov. 6, 2012

(54) METHOD OF FORMING OSELTAMIVIR AND DERIVATIVES THEREOF

(75) Inventors: Xuewei Liu, Singapore (SG); Jimei Ma, Singapore (SG)

(73) Assignee: Nanyang Technological University, Singapore (SG)

(*) Notice: Subject to any disclaimer, the term of this patent is extended or adjusted under 35 U.S.C. 154(b) by 63 days.

(21) Appl. No.: 12/809,521

(22) PCT Filed: Dec. 10, 2008

(86) PCT No.: PCT/SG2008/000473
§ 371 (c)(1),
(2), (4) Date: Oct. 4, 2010

(87) PCT Pub. No.: WO2009/078813
PCT Pub. Date: Jun. 25, 2009

(65) Prior Publication Data
US 2011/0021762 A1    Jan. 27, 2011

Related U.S. Application Data

(60) Provisional application No. 61/014,856, filed on Dec. 19, 2007.

(51) Int. Cl.
C07D 231/04 (2006.01)
C07D 263/52 (2006.01)
C07F 7/02 (2006.01)
C07F 7/04 (2006.01)
C07C 61/08 (2006.01)

(52) U.S. Cl. ........ 548/110; 548/221; 556/410; 556/418; 556/442; 560/125; 562/507; 562/508

(58) Field of Classification Search .................. 548/110, 548/221; 556/410, 418, 442; 560/125; 562/507, 562/508
See application file for complete search history.

(56) References Cited

FOREIGN PATENT DOCUMENTS
KR    10-2007-0082985    8/2007

OTHER PUBLICATIONS

Allenmark, "Chiroptical methods in the stereochemical analysis of natural products" Nat. Prod. Rep. 17: 145-155, 2000.
Agnihotri et al., "Mild and efficient method for the cleavage of benzylidene acetals using $HClO_4$-$SiO_2$ and direct conversion of acetals to acetates" Tetrahedron Letters 47: 3653-3658, 2006.

(Continued)

*Primary Examiner* — Joseph K. McKane
*Assistant Examiner* — Samantha Shterengarts
(74) *Attorney, Agent, or Firm* — Seed IP Law Group PLLC

(57) ABSTRACT

A process is provided for the synthesis of 4,5-diamino cyclohexene carboxylate ester (1): or a pharmaceutically acceptable salt thereof. $R^1$-$R^3$ are a silyl-, an aliphatic, alicyclic, aromatic, arylaliphatic, or an arylalicyclic group. $R^4$, $R^{11}$ and $R^{12}$ are H, a silyl-group, an aliphatic, alicyclic, aromatic, arylaliphatic, or an arylalicyclic group. 3,4-Dihydropyran compound (9): with $R^5$ and $R^6$ being suitable protecting groups, is reacted to form aldehyde (4): which is oxidized and converted to N-substituted carbamate (3): with $R^7$ being a suitable protecting group. (3) is, via oxazolinidone (13): converted to azido carboxylate ester (2): and then to 4,5-diamino cyclohexene carboxylate ester (1).

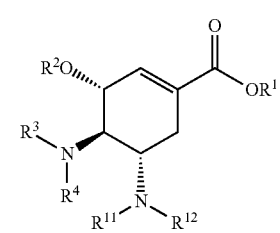

(1)

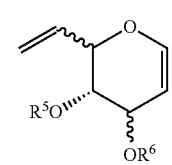

(9)

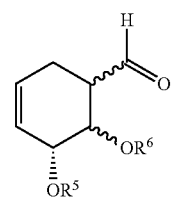

(4)

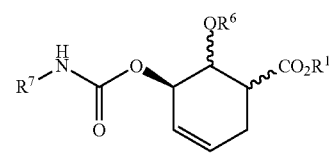

(3)

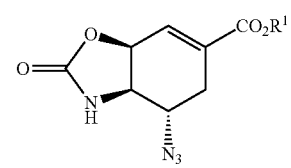

(13)

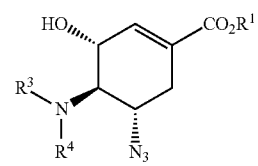

(2)

21 Claims, 9 Drawing Sheets

OTHER PUBLICATIONS

Ando, "Authorities in Taiwan Issue Compulsory Licence for Tamiflu, Roche Responds with Supply Promise" Word Markets Analysis, Nov. 29, 2005, 3 pages.

Bradsher et al., "Pressure Rises on Producer of a Flu Drug" The New York Times, Oct. 11, 2005, Late Edition, 4 pages.

Brown, "Run on Drug for Avian Flu Has Physicians Worried" The Washington Port, Oct. 22, 2005, Final Edition, 4 pages.

"Roche expands Tamiflu manufacturing network" Chemical News & Intelligence, Mar. 16, 2006, 2 pages.

Cong et al., "Ring-Closing Metathesis-Based Synthesis of (3R,4R,5S)-4-Acetylamino-5-amino-3-hydroxycyclohex-1-ene-carboxylic Acid Ethyl Ester: A Functionalized Cycloalkene Skeleton of GS4104" J. Org. Chem. 71: 5365-5368, 2006.

Du et al., "The First Total Synthesis of Sporiolide A" J. Org. Chem. 71: 8446-8451, 2006.

Farina et al., "Tamiflu: The Supply Problem" Angew. Chem. Int. Ed. 45: 7330-7334, 2006.

Fukuta et al., "De Novo Synthesis of Tamiflu via a Catalytic Asymmetric Ring-Opening of *meso*-Aziridines with $TMSN_3$" J. Am. Chem. Soc. 128: 6312-6313, 2006.

Harper et al., "Stereochemical Analysis by Solid-State NMR: Structural Predications in Ambuic Acid" J. Org. Chem. 68: 4609-4614, 2003.

Jarowicki et al., "Protecting groups" J. Chem. Soc., Perkin Trans. 1: 1589-1615, 1999.

Jarowicki et al., "Protecting groups" J. Chem. Soc., Perkin Trans. 1: 2109-2135, 2001.

Liu et al., "Copper-Catalyzed Tethered Aziridination of Unsaturated N-Tosyloxy Carbamates" J. Org. Chem. 72: 5587-5591, 2007.

Mita et al., "Second Generation Catalytic Asymmetric Synthesis of Tamiflu: Allylic Substitution Route" Organic Letters 9(2): 259-262, 2007.

Pine et al., "Organic Chemistry: $4^{th}$ Edition" McGraw-Hill Book Company, Singapore, 1981, pp. 97-99, 115-119.

Riccio et al., "Stereochemical analysis of natural products. Approaches relying on the combination of NMR spectroscopy and computational methods" Pure Appl. Chem. 75(2-3): 295-308, 2003.

Rohloff et al., "Practical Total Synthesis of the Anti-Influenza Drug GS-4104" J. Org. Chem. 63: 4545-4550, 1998.

Satoh et al., "A Practical Synthesis of ( − )-Oseltamivir" Angew. Chem. Int. Ed. 46: 5734-5736, 2007.

Shie et al., "Synthesis of Tamiflu and its Phosphonate Congeners Possessing Potent Anti-Influenza Activity" J. Am. Chem. Soc. 129: 11892-11893, 2007.

Spivey et al., "Synthetic methods Part (v) Protecting Groups" Annu. Rep. Prog. Chem., Sect. B 95: 83-95, 1995.

Tsunoda et al., "A Facile Procedure for Acetalization Under Aprotic Conditions" Tetrahedron Letters 21: 1357-1358, 1980.

Von Itzstein, "The war against influenza: discovery and development of sialidase inhibitors" Nature Reviews Drug Discovery 6: 967-974, 2007.

Wright, "Roche bends to pressure on flu drug demand" The International Herald Tribune, Nov. 11, 2005, 3 pages.

Wuts et al., "Greene's Protective Groups in Organic Synthesis" John Wiley & Sons, Inc., 2007, pp. 1-15.

Yamatsugu et al., "A concise synthesis of Tamiflu: third generation route via the Diels-Alder reaction and the Curtius rearrangement" Tetrahedron Letters 48: 1403-1406, 2007.

Yeung et al., "A Short Enantioselective Pathway for the Synthesis of the Anti-Influenza Neuramidase Inhibitor Oseltamivir from 1,3-Butadiene and Acrylic Acid" J. Am. Chem. Soc. 128: 6310-6311, 2006.

Route 2:

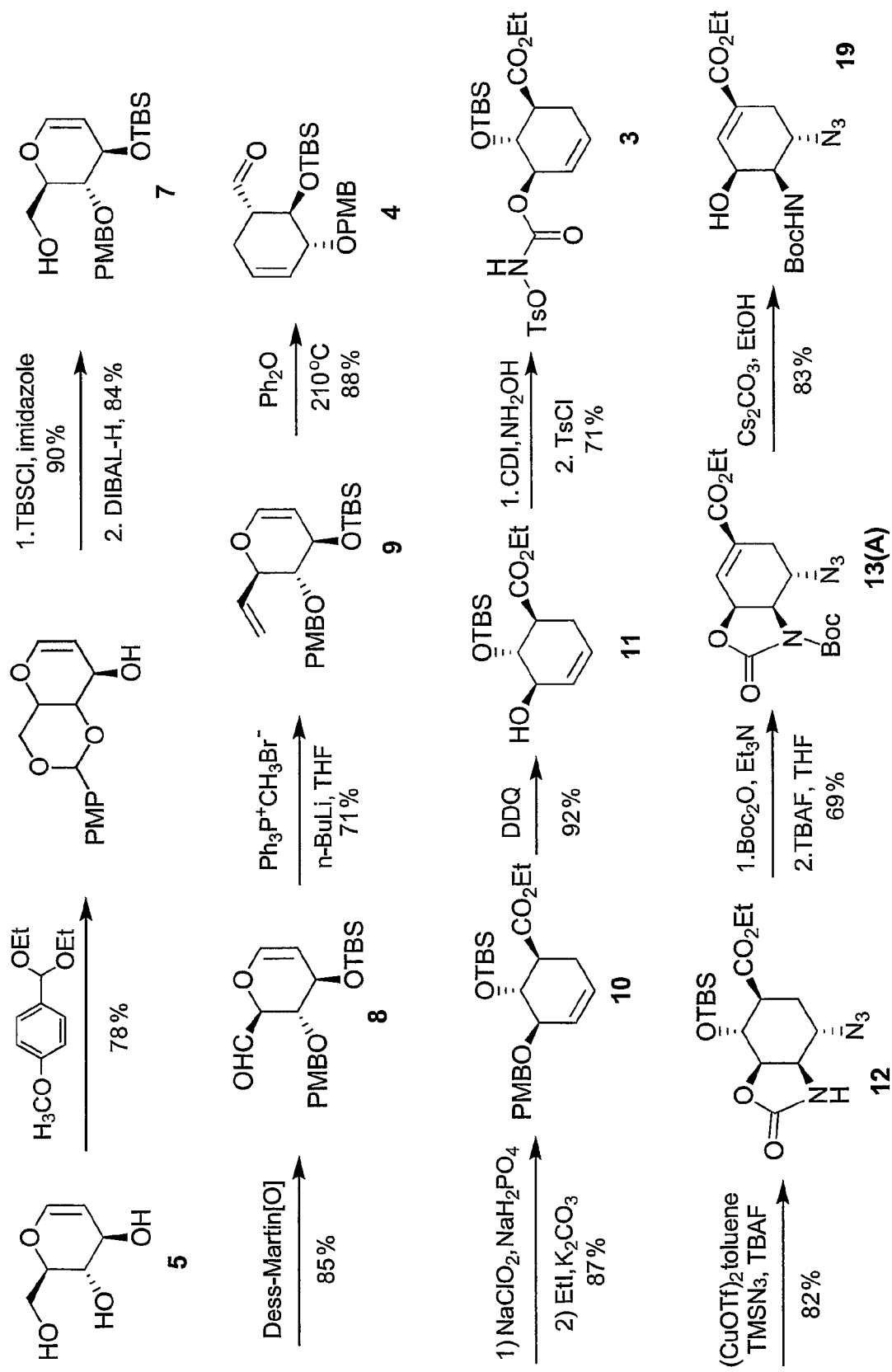
Fig. 9 (cont. on next page)

METHOD OF FORMING OSELTAMIVIR AND DERIVATIVES THEREOF

This application makes reference to and claims the benefit of priority of an application for a "Method Of Forming Oseltamivir And Derivatives Thereof" filed on Dec. 19, 2007 with the United States Patent and Trademark Office, and there duly assigned Ser. No. 61/014,856. The contents of said application filed on is incorporated herein by reference for all purposes, including an incorporation of any element or part of the description, claims or drawings not contained herein and referred to in Rule 20.5(a) of the PCT, pursuant to Rule 4.18 of the PCT.

FIELD OF THE INVENTION

The present invention relates to the stereoselective synthesis of Oseltamivir and derivatives thereof. Also provided are compounds useful in the synthesis.

BACKGROUND OF THE INVENTION

Oseltamivir, and in particular its phosphate salt, is a potent inhibitor of neuraminidases (for an introduction see e.g. von Itzstein, M., *Nature Reviews Drug Discovery* (2007) 6, 12, 967-974) and is currently the best drug among the currently available anti-influenza treatments due to its good oral bioavailablity and tolerance. It acts to minimise the effects of flu by inhibiting the protein neuraminidase that lives on the flu virus cells. Oseltamivir was developed by Gilead Sciences, and it is currently marketed by Hoffman La Roche under the tradename Tamiflu. Influenza causes 20,000-40,000 deaths per year in the US alone. Additionally, the recent spread of the avian virus strain H5N1, found in birds and poultry ('bird flu', or 'avian flu'), is causing great concern worldwide due to its severity with a lethality rate in humans of over 50%. According to the World Health Organization, about 200 deaths around the world since late 2003 had been officially attributed to H5N1 as of 2007. As the virus has become endemic in countries such as Indonesia and Vietnam there is fear that H5N1 will turn into a human form of influenza virus, giving rise to a pandemic.

Countries around the world have sought to stockpile Tamiflu against the possibility of global outbreak of a form of the avian virus that could be spread by humans. In 2008 Singapore announced it had already purchased 1.05 million courses of Tamiflu and intended to add a further 650,000 courses, while the British government was quoted to hold sufficient quantities of Tamiflu to treat one-quarter of its population. In the same year a British government report warned that the world was ill-prepared for an inevitable influenza pandemic. The report further warned that while the last two pandemics—in 1958 and 1968—were caused by relatively mild strains of influenza the next one could have more serious consequences, especially if it originated from H5N1. Accordingly, stockpiling led to an expansion of the manufacturer's production capacity to 400 m treatments annually already by the end of 2006 (*Chemical News & Intelligence*: Roche expands Tamiflu manufacturing network, Mar. 16, 2006) and caused some jurisdictions to issue a compulsory licence (*World Markets Analysis*: Authorities in Taiwan Issue Compulsory Licence for Tamiflu, Roche Responds with Supply Promise, Nov. 29, 2005).

Efficient and scalable synthesis is the key to meet the increasing global demand for this drug. The current commercial synthetic route involves a 10-step process of complex chemical reactions (e.g. Rohloff, J. C., et al., *J. Org. Chem.* (1998) 63, 4545-4550) and requires a production time of more than six months (*The New York Times*: Pressure Rises On Producer Of a Flu Drug, Oct. 11, 2005; *The Washington Post*: Run on Drug for Avian Flu Has Physicians Worried, Oct. 22, 2005; Yeung, Y. Y., et al., *J. AM. Chem. Soc.* (2006) 128, 6310-6311) and uses naturally occurring (−)-shikimic acid as a starting material. However (−)-shikimic acid is expensive and of limited availability, two-thirds of the current supply originate from one single source obtained from the pods of the Chinese star anise. The remaining third is obtained by fermentating *E. coli* bacteria (*The International Herald Tribune*: Roche bends to pressure on flu drug demand, Nov. 11, 2005). There is therefore a need for alternative synthesis routes.

Hence, new synthesis routes starting from other materials have been extensively investigated (see e.g. Farina, V., & Brown, J. D., *Angew. Chem. Int. Ed.* (2006) 45, 7330-7334), carried out largely by well-established research groups of Corey (Yeung, Y. Y., et al., 2006, supra), Shibasaki (Fukuta, Y., et al., *J. AM. Chem. Soc.* (2006) 128, 6312-6313; Yamatsugu, K., et al., *Tetrahedron Lett.* (2007) 48, 1403-1406; Mita, T., et al., *Organic Lett.* (2007) 9, 2, 259-262) and Cong (Cong, X., & Yao, Z. Y., *J. Org. Chem.* (2006) 71, 3565-5368). Starting materials used for forming Oseltamivir or derivatives thereof are 1,3-butadiene and acrylic acid (Yeung, Y. Y., et al., 2006, supra), fumaryl chloride and 1-(tert.-butyldimethylsiloxy-)-1,3-butadiene (Yamatsugu et al., 2007), L-serine (Cong, & Yao, 2006, supra), 3-amino-3-deoxy-1,2-O-isopropylidene-α-D-ribofuranose (Shie, J.-J., et al., *J. AM. Chem. Soc.* (2007) 129, 11892-11893), meso-aziridine (Fukuta et al., 2006, supra; Mita et al., 2007, supra), pyridine (Satoh, N., et al., *Angew. Chem. Int. Ed.* (2007) 46, 5734-5736) and [3aS-(3aα,6β,7α,7aα)]-3a,6,7,7a-tetrahydro-6,7-dihydroxy-5-(hydroxymethyl)-2-benzoxazolone (abstract of Korean patent application 2007-082985). After the priority date of the present application, Trost & Zhang (*Angew. Chemie Int. Ed. Engl.* (2008) 47, 3759-3761) furthermore presented the synthesis of Oseltamivir from racemic 6-Oxabicyclo[3.2.1]oct-3-en-7-one and a group at Hoffmann-La Roche Ltd disclosed a synthesis starting from 2,6-dimethoxyphenol that involves an enantioselective hydrolysis using pig liver esterase (Zutter, U., et al., *J. Org. Chem.* (2008) 73, 13, 4895-4902).

It is an object of the present invention to offer an alternative process of forming Oseltamivir or derivatives thereof.

This object is solved by a synthesis route as defined in the appended claims. The synthesis route can make use of easily available starting materials.

SUMMARY OF THE INVENTION

In a first aspect the invention provides a process of forming a 4,5-diamino cyclohexene carboxylate ester of general formula (1)

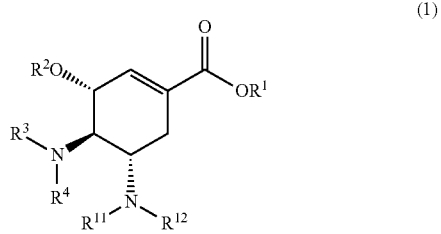

or a pharmaceutically acceptable salt thereof.

In general formula (1) and in other formulas used herein $R^1$-$R^3$ are independently from one another selected from a silyl-group, an aliphatic group, an alicyclic group, an aromatic group, an arylaliphatic group, and an arylalicyclic group, which may optionally include 0 to about 3 heteroatoms selected from the group N, O, S, Se and Si. $R^4$, $R^{11}$ and $R^{12}$ are independently from one another selected from the group H, a silyl-group, and an aliphatic, alicyclic, aromatic, arylaliphatic or an arylalicyclic group, which may optionally include 0 to about 3 heteroatoms selected from the group N, O, S, Se and Si.

The process of the first aspect the invention includes reacting a 3,4-dihydropyran compound (9)

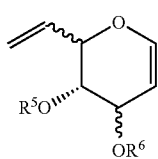

(9)

to form an aldehyde of general formula (4)

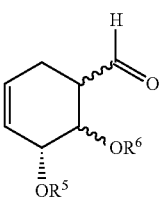

(4)

In general formula (4) as well as other formulas used herein $R^5$ and $R^6$ are independently selected suitable protecting groups and the symbol ∿ indicates that the respective bond may have any configuration.

The process of the first aspect the invention further includes oxidizing aldehyde (4) to carboxylic acid ester (10)

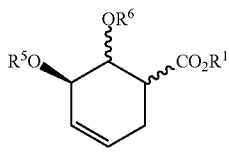

(10)

Furthermore, the process includes replacing protecting group $R^5$ of carboxylic acid ester (10) by an N-substituted carbamoyl group, thereby forming N-substituted carbamate (3)

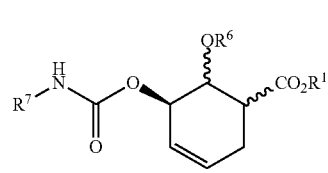

(3)

$R^7$ is a suitable protecting group. The process also includes reacting N-substituted carbamate (3) to form oxazolinidone (12)

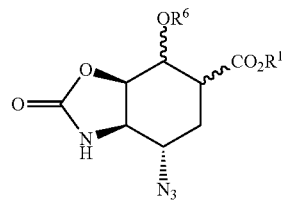

(12)

The process further includes removing moiety —$OR^6$ from oxazolinidone (12) to form oxazolinidone (13)

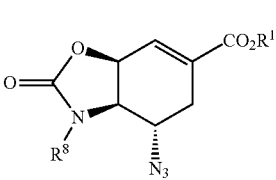

(13)

In general formula (13) as well as other formulas used herein $R^8$ is H or one of a silyl-group, an aliphatic group, an alicyclic group, an aromatic group, an arylaliphatic group, and an aryl-alicyclic group, that may include 0 to about 3 heteroatoms selected from the group N, O, S, Se and Si. Furthermore, the process includes reacting oxazolinidone (13) to form azido carboxylate ester (2)

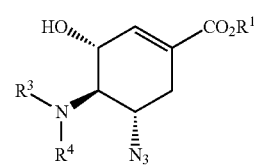

(2)

The process also includes converting azido carboxylate ester (2) to 4,5-diamino cyclohexene carboxylate ester (1).

In some embodiments $R^5$ consists of a methylene linker and a moiety $R^{10}$. In such embodiments the methylene linker connects moiety $R^{10}$ to the oxygen atom that defines the 4-hydroxy group of 3,4-dihydropyran compound (9), which may be an arabino-dienitol compound. $R^{10}$ is an aliphatic, alicyclic, aromatic, arylaliphatic, or arylalicyclic group, which may optionally include 0 to about 3 heteroatoms selected from the group N, O, S, Se and Si. In such embodiments 3,4-dihydropyran compound (9) can be represented by formula (9A)

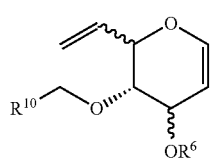

(9A)

The 3,4-dihydropyran compound (9A) can be obtained from 3,4-dihydropyran compound (5)

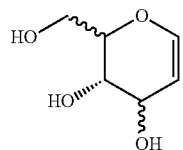

Thus the stereo-selective process of the invention provides a scalable synthetic route which is highly efficient and can be employed to utilize e.g. the inexpensive and commercially available glucal as a starting material.

In a second aspect the invention provides a compound of the formula (4)

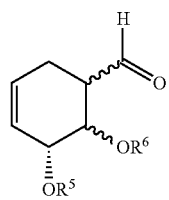

In formula (4) $R^5$ and $R^6$ are independently from one another selected suitable protecting groups or H, with the proviso that $R^5$ and $R^6$ are not both benzyl within the same molecule. The symbol $\sim$ indicates that the respective bond may have any configuration.

In a third aspect the invention provides a compound of the formula (10)

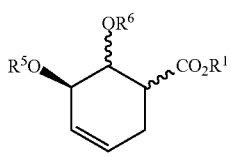

In formula (10) $R^1$ is selected from H, a silyl-group, an aliphatic, alicyclic, aromatic, arylaliphatic, or an arylalicyclic group that may optionally include 0 to about 3 heteroatoms selected from the group N, O, S, Se and Si. $R^5$ and $R^6$ are independently selected suitable protecting groups or H, with the proviso that $R^5$ and $R^6$ are not both acetyl within the same molecule. The symbol $\sim$ indicates that the bond may have any configuration.

In a fourth aspect the invention provides a compound of the formula (11)

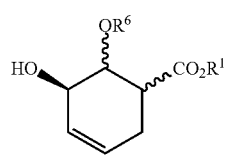

In formula (11) $R^1$ is selected from H, a silyl-group, an aliphatic, alicyclic, aromatic, arylaliphatic, or arylalicyclic group that may optionally include 0 to about 3 heteroatoms selected from the group N, O, S, Se and Si. $R^6$ is a suitable protecting group or H. The symbol $\sim$ indicates that the bond may have any configuration.

In a fifth aspect the invention provides a compound of the formula (12)

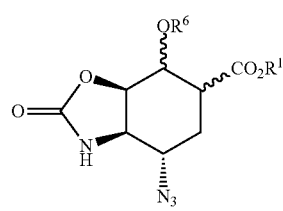

In formula (12) $R^1$ is selected from H, a silyl-group, an aliphatic, alicyclic, aromatic, arylaliphatic, or arylalicyclic group that may optionally include 0 to about 3 heteroatoms selected from the group N, O, S, Se and Si. $R^6$ is a suitable protecting group or H. The symbol $\sim$ indicates that the respective bond may have any configuration.

In a sixth aspect the invention provides a compound of the formula (13)

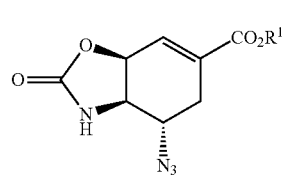

In formula (13) $R^1$ is selected from H, a silyl-group, an aliphatic, alicyclic, aromatic, arylaliphatic, or arylalicyclic group that includes 0 to about 3 heteroatoms selected from the group N, O, S, Se and Si. $R^6$ is a suitable protecting group or H.

In a seventh aspect the invention provides a compound of the formula (16)

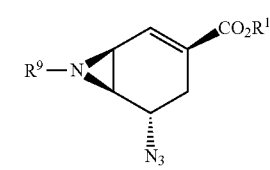

wherein $R^9$ is selected from the group consisting of a silyl-group, an aliphatic, an alicyclic, an aromatic, an arylaliphatic, and an arylalicyclic group, with the proviso that $R^1$ is not —C-Ph$_3$.

BRIEF DESCRIPTION OF THE DRAWINGS

The invention will be better understood with reference to the detailed description when considered in conjunction with the non-limiting examples and the accompanying drawings.

DETAILED DESCRIPTION OF THE INVENTION

Figure 1:
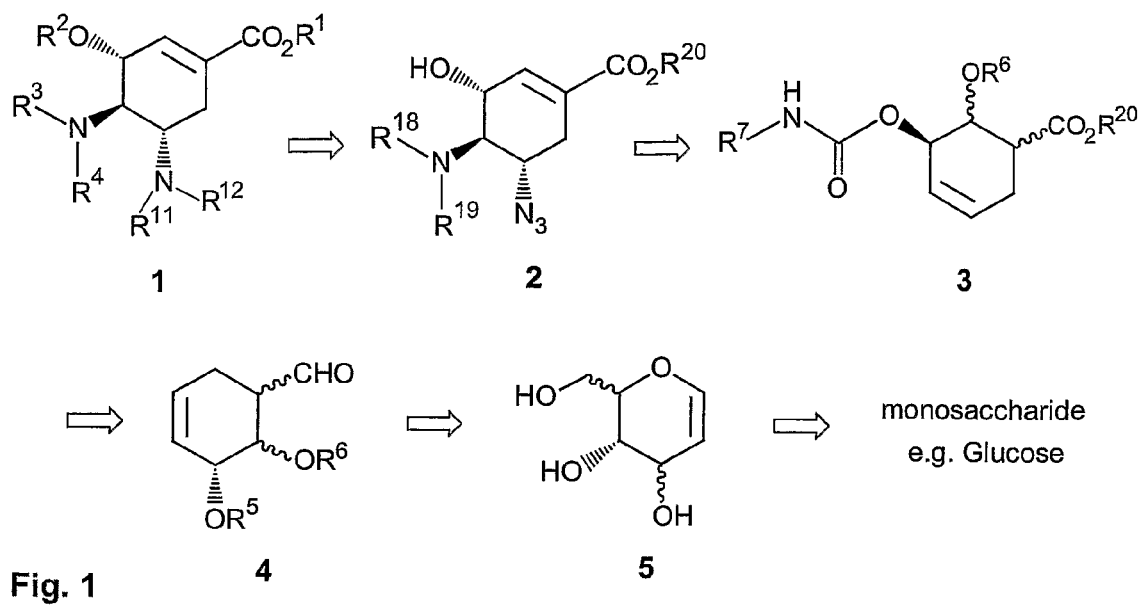
FIG. 1 depicts the retrosynthesis of Oseltamivir (1) and derivatives thereof.
Figure 2:
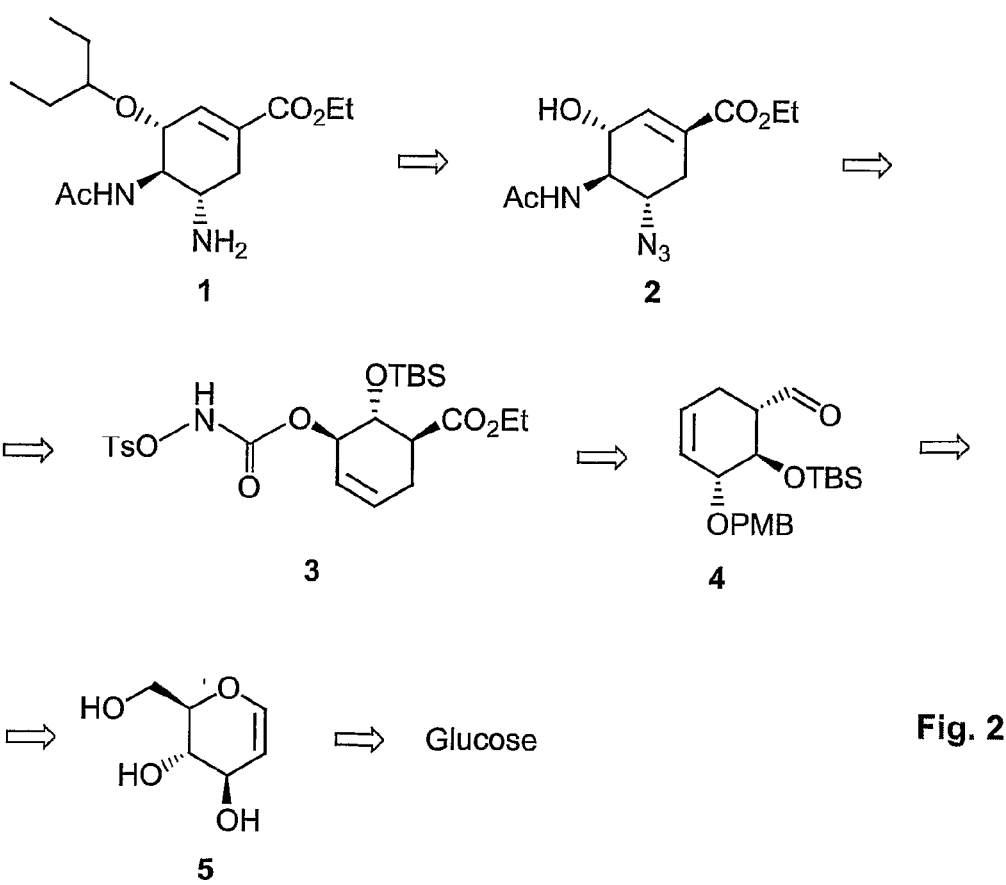
FIG. 2 depicts an exemplary embodiment of the retrosynthesis of Oseltamivir (1).
Figure 3:
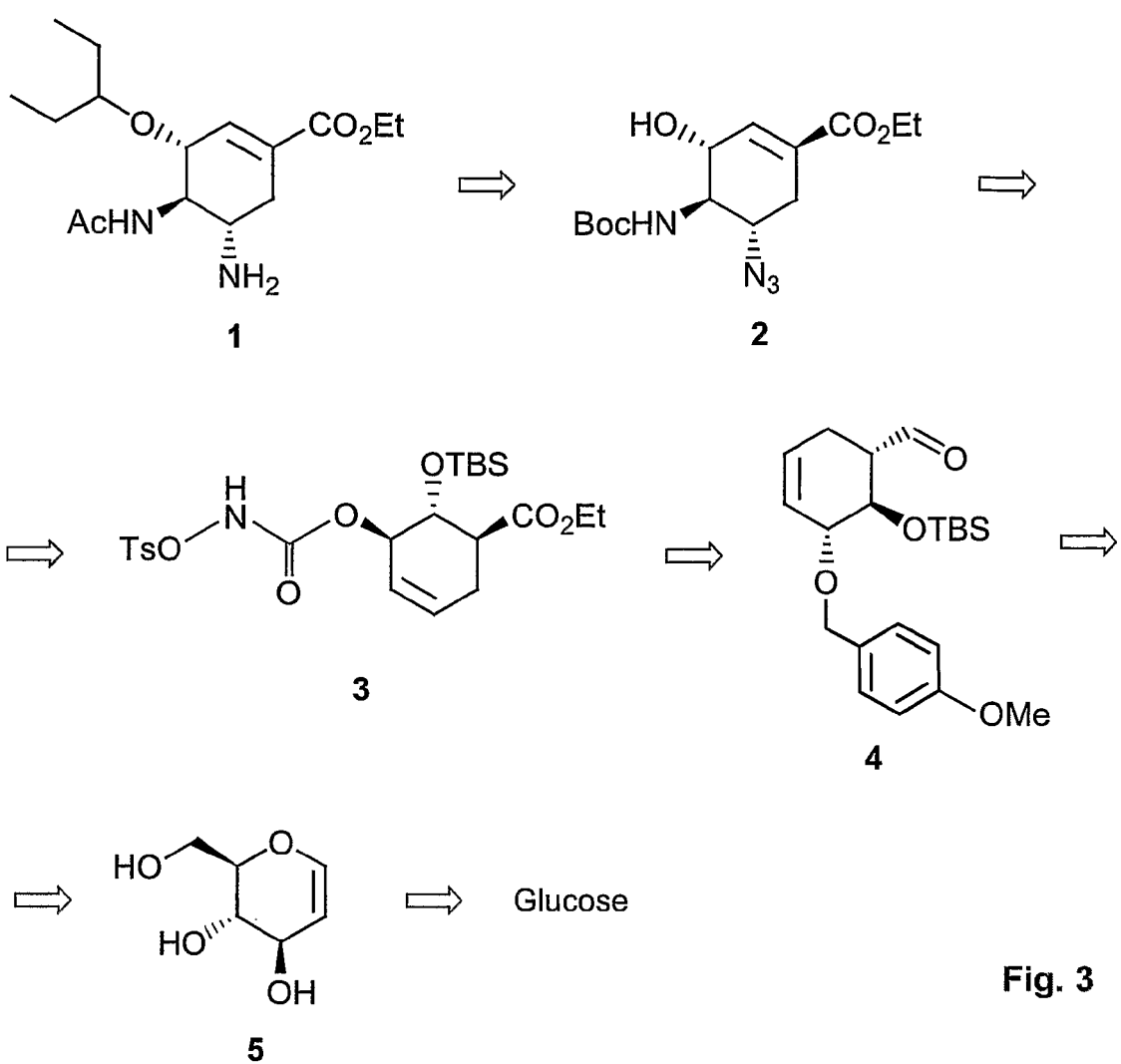
FIG. 3 depicts a further exemplary embodiment of the retrosynthesis of Oseltamivir (1).

As can be seen in FIG. 1, retrosynthetic analysis of the general synthesis route according to the present invention identifies N-substituted carbamate (3) as an important intermediate, which can be extended to azido carboxylate ester (2), the prototype of the target 4,5-diamino cyclohexene carboxylate ester (1) through the tandem intramolecular aziridination, ring-opening by N-containing nucleophiles and olefin formation upon treatment with base. The configurations at C4,5 can be set by taking advantage of the regioselectivity and stereoselectivity in the formation and ring-opening of the aziridine. N-substituted carbamate (3) can be derived from aldehyde (4) through novel transformations. The aldehyde (4) can be generated from 3,4-dihydropyran compound (5), employing a 3,3-sigmatropic rearrangement as a critical step to form a carbocycle with the desired chiral configurations at C2,3. 3,4-Dihydropyran compound (5) may for example be a glucal, a galactal or an idal. As a glucal, 3,4-dihydropyran compound (5) is for instance commercially available or can easily be synthesized from D-glucose. Two exemplary embodiments of the synthesis scheme of FIG. 1 are depicted in FIG. 2 and FIG. 3. As can be taken from a comparison of these two figures these embodiments differ in compound 2, where they have a different substituent $R^{18}$ (or alternatively $R^{19}$).

In cases where 3,4-dihydropyran compound (5) is the starting material (e.g. a glucal, a galactal or an idal) the 5- and the 6-hydroxy group as well as the 3-hydroxy group of 3,4-dihydropyran compound (5) can be protected, for example by anisaldehyde dimethylacetal and a silyl ether group respectively to form acetal (7) (see also FIG. 4), which can then be reduced to give 3,4-dihydropyran compound (8), for example by DIBAL-H. In other embodiments 3,4-dihydropyran compound (8) can be obtained by deprotecting a respective ether group (Du, Y., et al., *J. Org. Chem.* (2006) 71, 8446-8451).

The alcohol group of 3,4-dihydropyran compound (8) can be oxidized to an aldehyde and converted to 3,4-dihydropyran compound (9) by methylenation. Aldehyde (4) can then be obtained by Claisen rearrangement from 3,4-dihydropyran compound (9). The aldehyde (4) can be oxidized, for instance by Dess-Martin periodinane (1,1,1-triacetoxy-1,1-dihydro-1,2-benziodoxol-3(1H)-one) and transformed to carboxylic acid ester (10) by esterification. The protecting group $R^5$ of carboxylic acid ester (10) can then be replaced by an N-substituted carbamoyl group. For this purpose protecting group $R^5$ can for example be removed by a suitable reagent to afford hydroxy carboxylic acid ester (11). In this regard it may be advantageous to choose the two protecting groups $R^5$ and $R^6$ in such a manner that their sequential removal can be achieved, in particular that protecting group $R^5$ can be removed while $R^6$ remains intact. Hydroxy carboxylic acid ester (11) can for instance be reacted with CDI and $NH_2OH·HCl$, followed by e.g. tosylation to generate N-substituted carbamate (3).

Aziridination of N-substituted carbamate (3) and ring-opening, for instance by $TMSN_3$, can afford oxazolinidone (12), which can be treated with a Brønsted base to afford oxazolinidone (13). The carbamate can for example be converted to azido carboxylate ester (2) by acylating with an acyl anhydride and hydrolysis, e.g. by NaOMe. Protection of the 3-OH group of carboxylate ester (2), for instance with $Cl_3CC$ (=NH)OCHEt$_2$, can give azido carboxylate ester (14). Azido carboxylate ester (14) can then be reduced to 4,5-diamino cyclohexene carboxylate ester (1).

Figure 4:
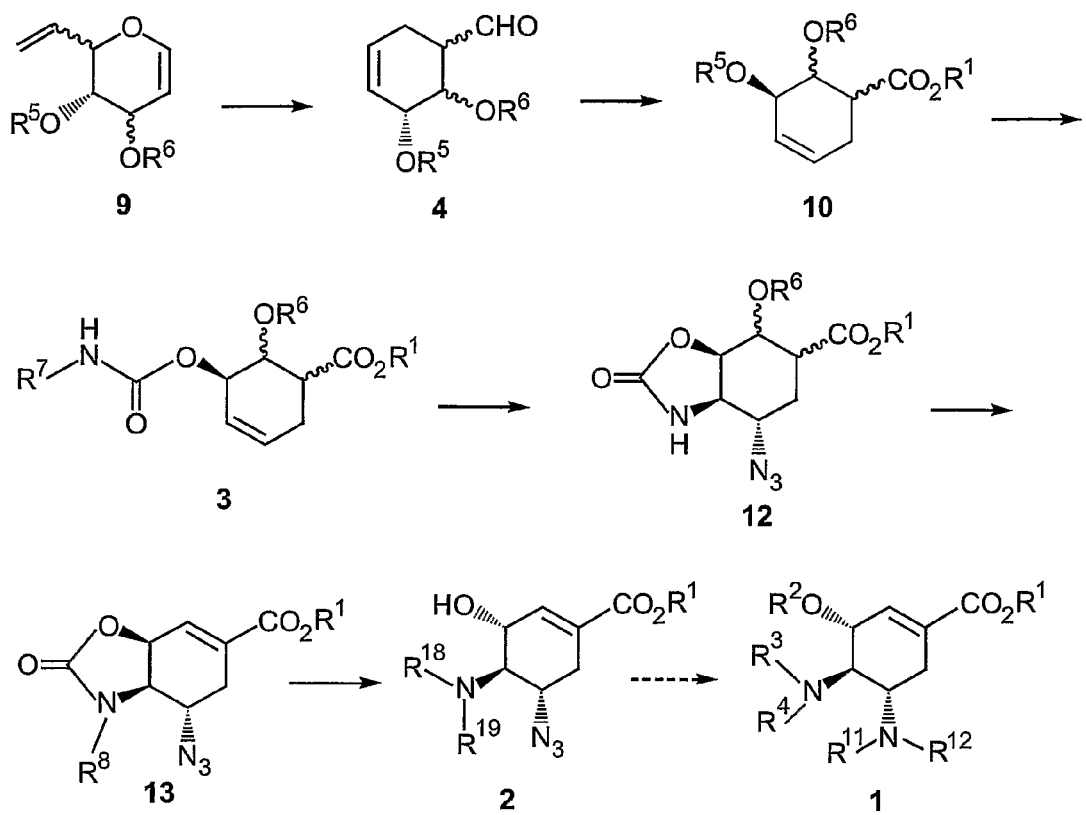
FIG. 4 shows the synthesis of Oseltamivir (1) and derivatives thereof.
Figure 5:
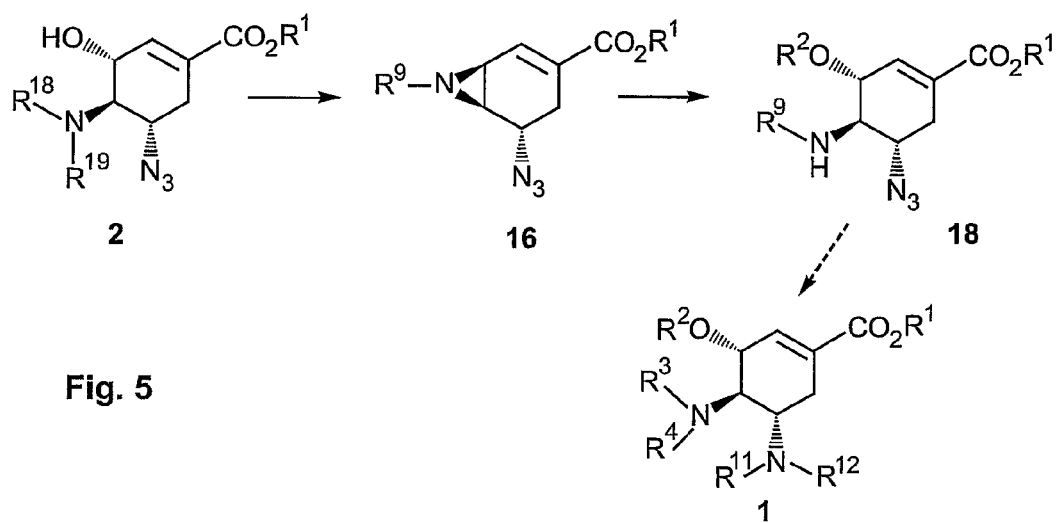
FIG. 5 depicts an exemplary synthesis path of the last step depicted in the general synthesis of FIG. 4.
Figure 6:
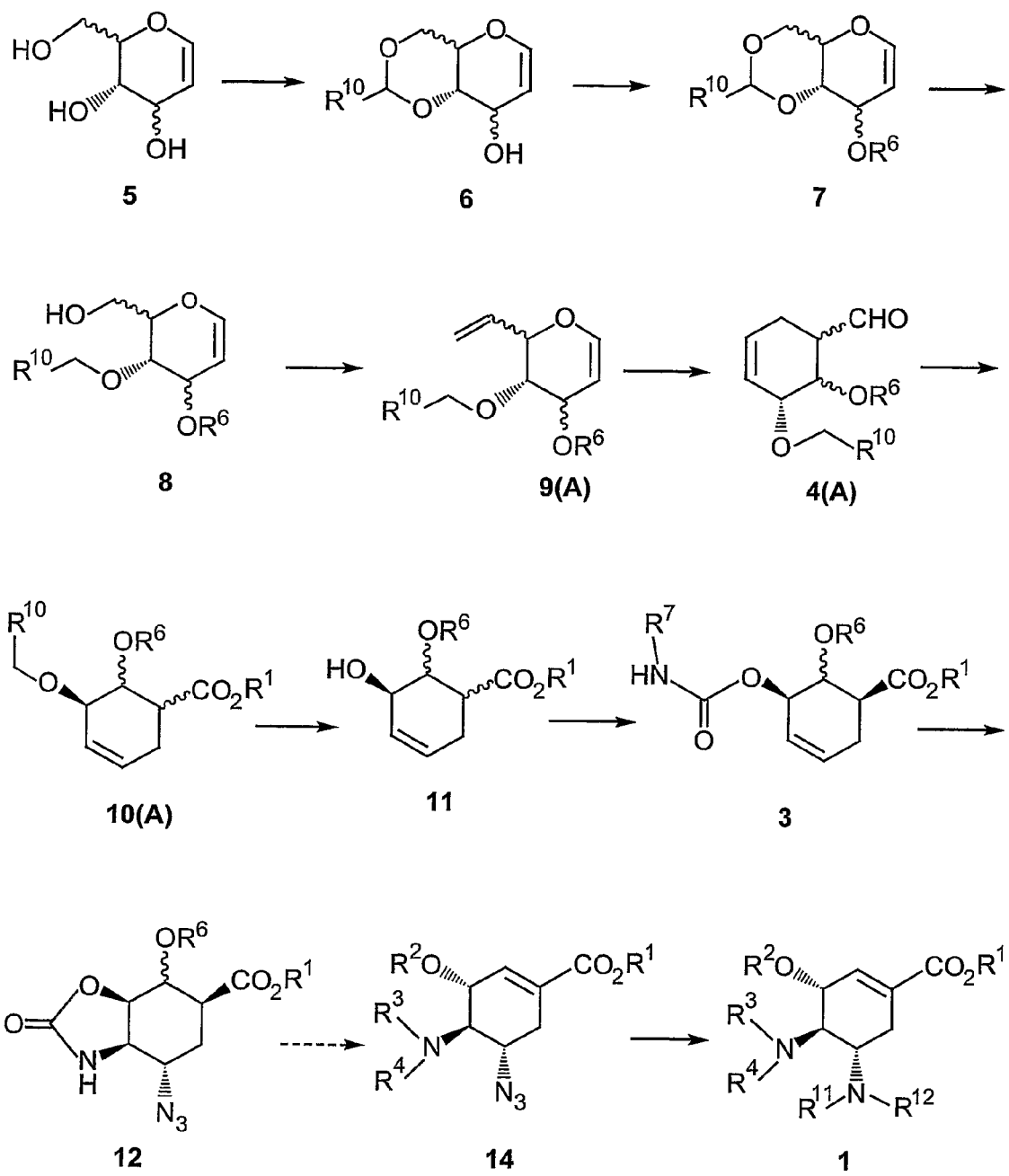
FIG. 6 depicts an exemplary scheme of the synthesis of a cyclohexene carboxylate ester (1).
Figure 9:
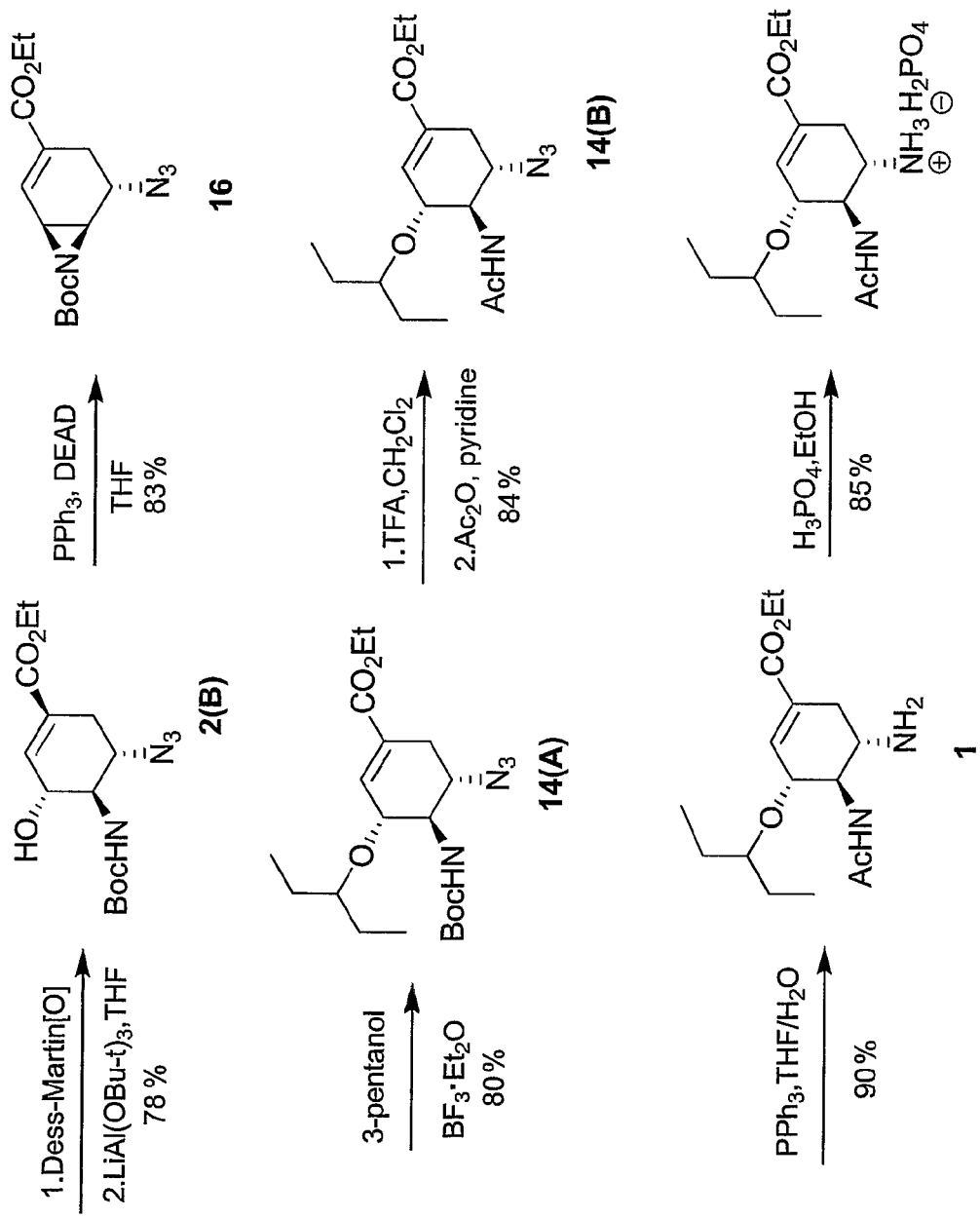
FIG. 9 depicts an exemplary embodiment of the synthesis of Oseltamivir Phosphate (1.$H_3PO_4$).

A general scheme of the synthesis of 4,5-diamino cyclohexene carboxylate ester (1) is shown in FIG. 4. An entire sequence of the synthesis starting from 3,4-dihydropyran compound (5) is shown in FIG. 6 and in FIG. 9. It is understood that the depicted synthesis can also be carried out with the isomers that represent mirror images of the depicted compounds.

The process of the invention provides a 4,5-diamino cyclohexene carboxylate ester of general formula (1)

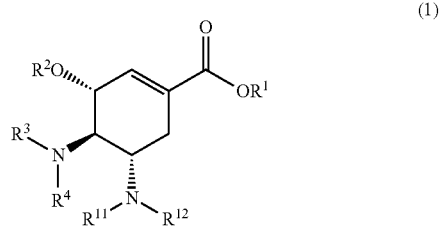

(1)

In this formula $R^1$, $R^2$ and $R^3$ are, independent from one another, a silyl-group, an aliphatic group, an alicyclic group, an aromatic group, an arylaliphatic group, or an arylalicyclic group. $R^4$, $R^{11}$ and $R^{12}$ are, independent from one another, H, a silyl-group, and an aliphatic group, an alicyclic group, an aromatic group, an arylaliphatic group, or an arylalicyclic group.

A respective aliphatic, alicyclic, aromatic, arylaliphatic or arylalicyclic group is typically of a main chain length of 1 to about 10, to about 15 or to about 20 carbon atoms. Each of $R^1$, $R^2$ and $R^3$, $R^4$, $R^{11}$ and $R^{12}$ (as well as $R^4$, $R^5$, $R^6$, $R^7$ and $R^{10}$, see below) may for example include 0 to about 3, such as one or two, heteroatoms selected from the group N, O, S, Se and Si. In typical embodiments the groups $R^1$, $R^2$, $R^5$, $R^6$, $R^7$ and $R^{10}$ (see also below) are connected to the respective oxygen atom, and $R^3$, $R^4$, $R^{11}$ and $R^{12}$, to the respective nitrogen atom, via a carbon or a silicon atom.

The term "aliphatic" means, unless otherwise stated, a straight or branched hydro-carbon chain, which may be saturated or mono- or poly-unsaturated and include heteroatoms (see below). An unsaturated aliphatic group contains one or more double and/or triple bonds (alkenyl or alkinyl moieties). The branches of the hydrocarbon chain may include linear chains as well as non-aromatic cyclic elements. The hydrocarbon chain, which may, unless otherwise stated, be of any length, and contain any number of branches. Typically, the hydrocarbon (main) chain includes 1 to 5, to 10, to 15 or to 20 carbon atoms. Examples of alkenyl radicals are straight-chain or branched hydrocarbon radicals which contain one or more double bonds. Alkenyl radicals generally contain about two to about twenty carbon atoms and one or more, for instance two, double bonds, such as about two to about ten carbon atoms, and one double bond. Alkynyl radicals normally contain about two to about twenty carbon atoms and one or more, for example two, triple bonds, preferably such as two to ten carbon atoms, and one triple bond. Examples of alkynyl radicals are straight-chain or branched hydrocarbon radicals which contain one or more triple bonds. Examples of alkyl groups are methyl, ethyl, propyl, butyl, pentyl, hexyl, heptyl, octyl, nonyl, decyl, the n isomers of these radicals, isopropyl, isobutyl, isopentyl, sec-butyl, tent-butyl, neopentyl, 3,3 dimethylbutyl. Both the main chain as well as the branches may furthermore contain heteroatoms as for instance N, O, S, Se or Si or carbon atoms may be replaced by these heteroatoms.

The term "alicyclic" means, unless otherwise stated, a non-aromatic cyclic moiety (e.g. hydrocarbon moiety), which may be saturated or mono- or poly-unsaturated. The cyclic hydrocarbon moiety may also include fused cyclic ring systems such as decalin and may also be substituted with non-aromatic cyclic as well as chain elements. The main chain of the cyclic hydrocarbon moiety may, unless otherwise stated, be of any length and contain any number of non-aromatic cyclic and chain elements. Typically, the hydrocarbon (main) chain comprises includes 3, 4, 5, 6, 7 or 8 main chain atoms in one cycle. Examples of such moieties include, but are not limited to, cyclopentyl, cyclohexyl, cycloheptyl, or cyclooctyl. Both the cyclic hydrocarbon moiety and, if present, any cyclic and chain substituents may furthermore contain heteroatoms, as for instance N, O, S, Se or Si, or a carbon atom may be replaced by these heteroatoms. The term "alicyclic" also includes cycloalkenyl moieties which that are unsaturated cyclic hydrocarbons, which generally contain about three to about eight ring carbon atoms, for example five or six ring carbon atoms. Cycloalkenyl radicals typically have a double bond in the respective ring system. Cycloalkenyl radicals may in turn be substituted.

The term "aromatic" means, unless otherwise stated, a planar cyclic hydrocarbon moiety of conjugated double bonds, which may be a single ring or include multiple fused or covalently linked rings, for example, 2, 3 or 4 fused rings. The term aromatic also includes alkylaryl. Typically, the hydrocarbon (main) chain includes 5, 6, 7 or 8 main chain atoms in one cycle. Examples of such moieties include, but are not limited to, cylcopentadienyl, phenyl, naphthalenyl-, [10]annulenyl-(1,3,5,7,9-cyclodecapentaenyl-), [12]annulenyl-, [8]annulenyl-, phenalene (perinaphthene), 1,9-dihydropyrene, chrysene (1,2-benzophenanthrene). An example of an alkylaryl moiety is benzyl. The main chain of the cyclic hydrocarbon moiety may, unless otherwise stated, be of any length and contain any number of heteroatoms, as for instance N, O and S. Examples of such heteroaromatic moieties (which are known to the person skilled in the art) include, but are not limited to, furanyl-, thiophenyl-, naphtyl-, naphthofuranyl-, anthrathiophenyl-, pyridinyl-, pyrrolyl-, quinolinyl, naphthoquinolinyl-, quinoxalinyl-, indolyl-, benzindolyl-, imidazolyl-, oxazolyl-, oxoninyl-, oxepinyl-, benzoxepinyl-, azepinyl-, thiepinyl-, selenepinyl-, thioninyl-, azecinyl-(azacyclodecapentaenyl-), diazecinyl-, azacyclododeca-1,3,5,7,9,11-hexaene-5,9-diyl-, azozinyl-, diazocinyl-, benzazocinyl-, azecinyl-, azaundecinyl-, thia[11]annulenyl-, oxacyclotrideca-2,4,6,8,10,12-hexaenyl- or triazaanthracenyl-moieties.

By the term "arylaliphatic" is meant a hydrocarbon moiety, in which one or more aromatic moieties are substituted with one or more aliphatic groups. Thus the term "arylaliphatic" also includes hydrocarbon moieties, in which two or more aryl groups are connected via one or more aliphatic chain or chains of any length, for instance a methylene group. Typically, the hydrocarbon (main) chain includes 5, 6, 7 or 8 main chain atoms in each ring of the aromatic moiety. Examples of arylaliphatic moieties include, but are not limited, to 1-ethyl-naphthalene, 1,1'-methylenebis-benzene, 9-isopropylanthracene, 1,2,3-trimethyl-benzene, 4-phenyl-2-buten-1-ol, 7-chloro-3-(1-methylethyl)-quinoline, 3-heptyl-furan, 6-[2-(2,5-diethylphenyl)ethyl]-4-ethyl-quinazoline or, 7,8-dibutyl-5,6-diethyl-isoquinoline.

Each of the terms "aliphatic", "alicyclic", "aromatic" and "arylaliphatic" as used herein is meant to include both substituted and unsubstituted forms of the respective moiety. Substituents my be any functional group, as for example, but not limited to, amino, amido, azido, carbonyl, carboxyl, cyano, isocyano, dithiane, halogen, hydroxyl, nitro, organometal, organoboron, seleno, silyl, silano, sulfonyl, thio, thiocyano, trifluoromethyl sulfonyl, p-toluenesulfonyl, bromobenzenesulfonyl, nitrobenzenesulfonyl, and methanesulfonyl.

A heteroatom is any atom that differs from carbon. Examples include, but are not limited to N, O, P, S, and Se. Were several heteroatoms are present within a moiety of a reactant or product of the process of the invention, they are independently selected.

In cyclohexene carboxylate ester (1) group $R^1$ is typically a carboxylic acid protecting group known in the art. The use of protecting groups is a well established technique in the art for various functional groups and a large number of protecting groups, well known to those skilled in the art, is available for numerous functional groups. Illustrative examples of a carboxylic acid protecting group are an alkyl, an alkenyl, and an alkynyl ester.

A further illustrative example is a silyl ester, in which $R^1$ is of the structure:

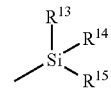

In such a silyl ester, groups $R^{13}$-$R^{15}$ are independently selected aliphatic, alicyclic, aromatic, arylaliphatic, or arylalicyclic groups, typically bonded to the Si-atom via a carbon atom (which is part of the respective group). In typical embodiments the carboxylic acid protecting group $R^1$ is connected to the oxygen atom of the ester group via a carbon or a silicon atom. Examples of a suitable carboxylic acid protecting group include, but are not limited to, methyl, substituted methyl (e.g. 9-fluorenylmethyl, methoxymethyl, methylthiomethyl, tetrahydropyranyl, tetrahydrofuranyl, methoxyethoxymethyl, 2-(trimethylsilyl)ethoxymethyl, benzyloxymethyl, phenacyl, p-bromophenacyl, α-methylphenacyl, p-methoxyphenacyl, carboxamidomethyl, N-phthalimidomethyl); ethyl, 2-substituted ethyl (2,2,2-trichloroethyl, 2-haloethyl, o-chloroalkyl, 2-(trimethylsilyl)ethyl, 2-methylthioethyl, 1,3-dithianyl-2-methyl, 2-(p-nitrophenylsulfenyl)ethyl, 2-(p-toluenesulfonyl)ethyl, 2-(2'-pyridyl)ethyl, 2-(diphenylphosphino)ethyl, 1-methyl-1-phenylethyl, tert.-butyl, cyclopentyl, cyclohexyl, allyl, 3-buten-1-yl, 4-(trimethylsilyl)-2-buten-1-yl, cinnamyl, α-methylcinnamyl, phenyl, p-(methylmercapto)phenyl, benzyl); substituted benzyl (e.g. triphenylmethyl, diphenylmethyl, bis(o-nitrophenyl)methyl, 9-anthrylmethyl, 2-(9,10-dioxo)anthrylmethyl, 5-dibenzosuberyl, 1-pyrenylmethyl, 2-(trifluoromethyl)-6-chromylmethyl, 2,4,6-trimethylbenzyl, p-bromobenzyl, o-nitrobenzyl, p-nitrobenzyl, p-methoxybenzyl, 2,6-dimethoxybenzyl, 4-(methylsulfinyl)benzyl, 4-sulfobenzyl, piperonyl, 4-picolyl, p-poly-benzyl); and silyl (trimethylsilyl, triethylsilyl, t-butyldimethylsilyl, iso-propyl-dimethylsilyl, phenyldimethylsilyl, di-tert.-butylmethylsilyl). In one embodiment 4,5-diamino cyclohexene carboxylate ester (1) is (3R,4R,5S)-4-(acetylamino)-5-amino-3-(1-ethylpropoxy)-1-cyclohexene-1-carboxylic acid ethyl ester (Chemical Abstracts No. 196618-13-0), or oseltamivir, which is represented by the following formula

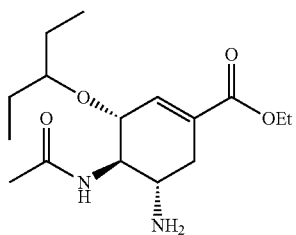

Protecting groups for the various functional groups described herein are well known in the art and frequently been summarized in form of books and reviews. Illustrative examples of suitable protecting groups for functional groups as described herein can for example be found in overviews published by Spivey and Maddaford (*Annu. Rep. Prog. Chem. Sect. B* (1999) 95, 83-95), Jarowicki and Kocienski (*J. Chem. Soc., Perkin Trans.* 1 (1999) 1589-1615; *J. Chem. Soc. Perkin Trans.* 1 (2001) 2109-2135), and by Wuts & Greene (Greene's Protective Groups in Organic Synthesis, Fourth Edition, Wiley & Sons, Inc., 1-15).

Further examples of a compound of general formula (1) include, but are not limited to, (3R,4R,5S)-4-(acetylamino)-5-amino-3-(2,3-dihydroxypropoxy)-1-cyclohexene-1-carboxylic acid methyl ester (Chemical Abstracts No. 208720-12-1), (3S,4R,5S,6S)-4-(acetylamino)-6-(acetyloxy)-3-[[(1,1-dimethylethoxy)carbonyl]amino]-5-(1-ethylpropoxy)-1-cyclohexene-1-carboxylic acid ethyl ester (CAS No. 208589-22-4), (3R,4R,5S)-5-amino-4-[(1-oxopropyl)amino]-3-propoxy-1-cyclohexene-1-carboxylic acid methyl ester (CAS No. 208720-65-4), (3R,4R,5S)-4-(acetylamino)-5-amino-3-[(1R)-1-methylpropoxy]-1-cyclohexene-1-carboxylic acid methyl ester (CAS No. 208720-68-7), (3R,4R,5S)-4-(acetylamino)-5-[[[[(1,1-dimethylethoxy)-carbonyl]amino][[(1,1-dimethylethoxy)carbonyl]methylamino]methylene]amino]-3-propoxy-1-cyclohexene-1-carboxylic acid methyl ester (CAS No. 208720-66-5), (3R,4R,5S)-4-(acetyl-amino)-5-amino-3-(1-ethylpropoxy)-1-cyclohexene-1-carboxylic acid methyl ester (CAS No. 208720-71-2), (3R,4R,5S)-4-(acetylamino)-5-amino-3-(1,1-dimethylpropoxy)-1-carboxylic acid methyl ester (CAS No. 208720-73-4), (3R,4R,5S)-4-(acetylamino)-5-amino-3-(methoxymethoxy)-1-cyclohexene-1-carboxylic acid methyl ester (CAS No. 208720-84-7), (3R,4R,5S)-4-(acetylamino)-3-(1-ethylpropoxy)-5-[(trifluoro acetyl)amino]-1-cyclohexene-1-carboxylic acid methyl ester (CAS No. 221386-89-6), (3R,4R,5S)-4-(acetylamino)-3-(1-ethylpropoxy)-5-[methyl(trifluoroacetyl)amino]-1-cyclohexene-1-carboxylic acid methyl ester (CAS No. 221386-90-9), (3R,4R,5S)-4-(acetylamino)-3-amino-5-(methoxymethoxy)-1-cyclohexene-1-carboxylic acid methyl ester (CAS No. 243472-90-4), (3R,4R,5S)-4-(acetylamino)-3-[[[[(1,1-dimethyl-ethoxy)carbonyl]amino]iminomethyl]amino]-5-(methoxymethoxy)-1-cyclohexene-1-carboxylic acid methyl ester (CAS No. 243472-91-5), (3R,4R,5S)-4-(acetylamino)-5-amino-3 [1-(carboxymethyl)propoxy]-1-cyclohexene-1-carboxylic acid methyl ester (CAS No. 252191-16-5), (3R,4R,5S)-4-(acetylamino)-5-amino-3-[(1R)-1-(carboxymethyl)propoxy]-1-cyclohexene-1-carboxylic acid 1-ethyl ester (CAS No. 252191-17-6), (3R,4R,5S)-4-(acetylamino)-5-amino-3-[(1S)-1-ethyl-3-hydroxypropoxy]-1-cyclohexene-1-carboxylic acid 1-ethyl ester (CAS No. 252191-19-8), (3R,4R,5S)-4-(acetylamino)-3-(1-ethylpropoxy)-5-(2-propenylamino)-1-cyclohexene-1-carboxylic acid ethyl ester (CAS No. 312904-18-0), (3R,4R,5S)-3-(1-ethylpropoxy)-4-[(phenylmethylene)amino]-5-(2-propenylamino)-1-cyclohexene-1-carboxylic acid ethyl ester (CAS No. 332047-19-5), (3R,4R,5S)-4-(acetylamino)-5-(acetyl-2-propenylamino)-3-(1-ethylpropoxy)-1-cyclohexene-1-carboxylic acid ethyl ester (CAS No. 332047-20-8), (3aR,4R,7aS)-4-(1-ethylpropoxy)-3a,4,7,7a-tetrahydro-2-methyl-1-(2-propenyl)-1H-benzimidazole-6-carboxylic acid ethyl ester (CAS No. 332047-21-9), (3R,4R,5S)-4-(acetylamino)-3-(1-ethylpropoxy)-5-(propylamino)-1-cyclohexene-1-carboxylic acid ethyl ester (CAS No. 332047-24-2), (3R,4R,5S)-4-(acetylamino)-5-[[(1,1-dimethylethoxy)carbonyl]amino]-3-(1-ethylpropoxy)-1-cyclohexene-1-carboxylic acid ethyl ester (CAS No. 367252-68-4), (3R,4R,5S)-4-(acetylamino)-5-amino-3-(1-ethylpropoxy)-1-cyclohexene-1-carboxylic acid tetradecyl ester (CAS No. 371193-37-2), (3R,4R,5S)-4-(acetylamino)-3-(acetyloxy)-5-[[(1,1-dimethylethoxy)carbonyl]amino]-1-cyclohexene-1-carboxylic acid methyl ester (CAS No. 518003-70-8), (3R,4R,5S)-4-[(1,1-dimethylethyl)amino]-5-(di-2-propen-1-ylamino)-3-(1-ethylpropoxy)-1-cyclohexene-1-carboxylic acid ethyl ester (CAS No. 651324-06-0), (3R,4R,5S)-4-[acetyl(1,1-dimethylethyl)-amino]-5-(di-2-propenylamino)-3-(1-ethylpropoxy)-1-cyclohexene-1-carboxylic acid ethyl ester (CAS No. 651324-07-1), (3R,4R,5S)-4-[[(1,1-dimethylethoxy)carbonyl]amino]-3-(methoxymethoxy)-5-[[(phenylmethoxy)carbonyl]amino]-1-cyclohexene-1-carboxylic acid ethyl ester (CAS No. 903907-89-1), (3R,4R,5S)-4-[[(1,1-dimethylethoxy)carbonyl]amino]-3-(1-ethylpropoxy)-5-[[(2-propen-1-yloxy)carbonyl]amino]-1-cyclohexene-1-carboxylic acid ethyl ester (CAS No. 950896-07-8), (3R,4R,5S)-4-(acetylamino)-3-(1-ethylpropoxy)-5-[[(2-propen-1-yloxy)-carbonyl]amino]-1-cyclohexene-1-carboxylic acid ethyl ester (CAS No. 950896-08-9), (3R,4R,5S)-4,5-bis[[(1,1-dimethylethoxy)carbonyl]amino]-3-(1-ethylpropoxy)-1-cyclohexene-1-carboxylic acid ethyl ester (CAS No. 1012815-01-8), (3R,4R,5S)-4-(acetylamino)-5-(1,3-dihydro-1,3-dioxo-2H-isoindol-2-yl)-3-(1-ethylpropoxy)-1-cyclohexene-1-carboxylic acid ethyl ester (CAS No. 1041262-68-3), (3R,4R,5S)-4-(acetylamino)-5-amino-3-(1-methylethoxy)-1-cyclohexene-1-carboxylic acid ethyl ester (CAS No. 1052063-36-1), (3R,4R,5S)-4-(acetylamino)-5-amino-3-(1-methylpropoxy)-1-cyclohexene-1-carboxylic acid ethyl ester (CAS No. 105 2063-37-2), (3S,4R,5R)-4-(acetylamino)-3-amino-5-(1-ethylpropoxy)-1-cyclohexene-1-carboxylic acid ethyl ester (CAS No. 1052063-39-4), (3R,4R,5S)-5-amino-3-(1-ethylpropoxy)-4-[(1-oxopropyl)amino]-1-cyclohexene-1-carboxylic acid methyl ester (CAS No. 1052063-40-7), (3R,4R,5S)-4-(acetylamino)-5-[[(cyanoamino)iminomethyl]amino]-3-(1-ethylpropoxy)-1-cyclohexene-1-carboxylic acid ethyl ester (CAS No. 1058728-99-6) or the compound of CAS No. 1058729-00-2.

The process of the invention may also provide a pharmaceutically acceptable salt or a solvate of the 4,5-diamino cyclohexene carboxylate ester of general formula (1). Pharmaceutically acceptable salts include those obtained by reacting 4,5-diamino cyclohexene carboxylate ester (1), functioning as a base with an inorganic or organic acid to form a salt, for example, salts of hydrochloric acid, sulfuric acid, phosphoric acid, methane sulfonic acid, citric acid, camphor sulfonic acid, oxalic acid, maleic acid, succinic acid, citric acid, formic acid, hydrobromic acid, benzoic acid, tartaric acid, fumaric acid, salicylic acid, mandelic acid, and carbonic acid. The free amine can be used to form the pharmaceutically acceptable salt form, e.g. by reaction of compound (1) with the appropriate inorganic or organic acid, by conventional methods known in the art. The following are further examples of acid salts that can be obtained by reaction with inorganic or organic acids: acetates, adipates, alginates, citrates, aspartates, benzoates, benzenesulfonates, bisulfates, butyrates, camphorates, digluconates, cyclopeantanepropionates, dodecylsulfates, ethanesulfonates, glucoheptanoates, glycerophosphates, hemisulfates, heptanoates, hexanoates, fumarates, hydrobromides, hydroiodides, 2-hydroxyethanesulfonates, lactates, maleates, methanesulfonates, nicotinates, 2-naphthalene-sulfonates, oxalates, palmoates, pectinates, persulfates, 3-phenylpropionates, picrates, pivalates, propionates, succinates, tartrates, thiocyanates, tosylates, mesylates and undecanoates. In some embodiments the pharmaceutically acceptable salt is a sulphate or a phosphate. In typical embodiments a salt formed is pharmaceutically acceptable for administration to a mammal, including a human.

The term "pharmaceutically acceptable" as used herein refers to the property of matter to be administered, e.g. compositions, carriers, diluents or active compounds, as being capable of administration to or upon a human at least essentially without giving rise to undesirable physiological effects such as nausea, dizziness or gastric upset in the dose or amount used. In particular, the used amount or dose of such matter does not cause such effects to a degree that would prohibit administration of the composition. A pharmaceutically acceptable salt is nontoxic to the cell or mammal being exposed thereto at the dosages and concentrations employed.

The process includes reacting an 3,4-dihydropyran compound (9)

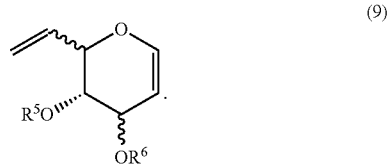

(9)

Throughout the specification the well established wedge representation is used to define the stereochemical configuration of the compounds referred to. The wedge representation defines one orientation of a substituent relative to another substituent and relative to a ring structure (see e.g. Pine, Hendrickson, Cram, Hammond: Organic Chemistry, McGraw-Hill, 4th edition, 1981, pages 97-99 & 115-119). By defining nonsuperimposable mirror images the absolute stereochemistry can accordingly be derived from the respective wedge representation. The R,S system of nomenclature can however in a number of cases not appropriately be applied to the depicted compounds, since this system is based on the ranking of substituents, e.g. H<C<N<O or $CH_3$-<$C_2H_5$-<$CH_2$=CH—. As an example, according to the R,S system of nomenclature a compound may in some embodiments termed the (S,S)- and in some embodiments the (R,R)-enantiomer, depending on the selected substituents of a specific embodiment. As an illustrative example, the azido compound of Chemical Abstracts No 208720-39-2 has an absolute configuration described as (3S,4R,5R), whereas the azido compounds of Chemical Abstracts Nos 221386-82-9 and 208720-40-5 have an absolute configuration described as (1R,5S,6R), as can also be taken from the examples of compound (14) below. Regardless of this difference in nomenclature, the absolute configuration of these compounds is the same.

It is nevertheless noted that 4,5-diamino cyclohexene carboxylate ester (1) typically has an absolute configuration that can be defined as (3R,4R,5S). The stereochemistry of the reactants and reaction products may be analysed according to any method known in the art, such as for instance 2D-NMR based on homo- or heteronuclear J-coupling values (Riccio, R., et al., Pure Appl. Chem. (2003) 75, 2-3, 295-308), electron ionisation mass spectrometry, polarimetry, circular dichroism spectroscopy (e.g. using the split Cotton-effect based on the Davydov splitting, see e.g. Allemark, S. G., Nat. Prod. Rep. (2000) 17, 145-155), enantio-selective chromatography, derivatisation in combination with standard analytical techniques such as NMR, including any suitable 2D-NMR technique, for example based on the nuclear Overhauser effect, as well as X-ray crystallography or solid state NMR (see e.g. Harper, J. K., et al., J. Org. Chem. (2003) 68, 4609-4614).

In this regard the symbol ∿ indicates that the respective bond may have any configuration. Any respective stereoisomer or a mixture of such stereoisomers in any desired ratio may be used. 3,4-Dihydropyran compound (9) may for instance be an arabino-dienitol compound. It may for example be used in the following embodiments:

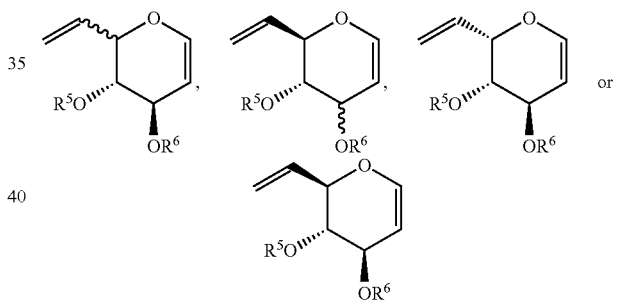

$R^5$ and $R^6$ are independently selected hydroxyl protecting groups. In typical embodiments the carboxylic acid protecting group $R^1$ is connected to the oxygen atom of the ester group via a carbon or a silicon atom (which is part of the respective group). A silyl ether group may be of the structure described above for a silyl ester, i.e. include groups $R^{13}$-$R^{15}$ (supra). Examples of a suitable hydroxyl protecting group include, but are not limited to, methyl ethers; substituted methyl ethers (e.g. methoxymethyl, methylthiomethyl, tert.-butylthiomethyl, (phenyldimethylsilyl)methoxymethyl, benzyloxymethyl, p-methoxybenzyloxymethyl, (4-methoxyphenoxy)methyl, guaiacolmethyl, tert.-butoxymethyl, 4-pentenyloxymethyl, siloxymethyl, 2-methoxyethoxymethyl, 2,2,2-trichloroethoxymethyl, bis(2-chloroethoxy)methyl, 2-(trimethylsilyl)ethoxymethyl, tetrahydropyranyl, 3-bromotetrahydropyranyl, tetrahydropthiopyranyl, 1-methoxycyclohexyl, 4-methoxytetrahydropyranyl, 4-methoxytetrahydrothiopyranyl, 4-methoxytetrahydropthiopyranyl S,S-dioxido, 1-[(2-chloro-4-methyl)phenyl]-4-methoxypiperidin-4-yl, 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl)); substituted ethyl ethers (1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, tert.-butyl, allyl, p-chlorophenyl, p-methoxyphenyl, 2,4-dinitrophenyl, benzyl); substituted benzyl bthers (p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2- and 4-picolyl, 3-methyl-2-picolyl N-oxido, diphenylmethyl, p,p'-dinitrobenzhydryl, 5-dibenzosuberyl, triphenylmethyl, a-naphthyldiphenylmethyl, p-methoxyphenyldiphenylmethyl, di(p-methoxyphenyl)phenylmethyl, tri(p-methoxyphenyl)methyl, 4-(4'-bromophenacyloxy)phenyldiphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-ylmethyl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido); silyl ethers (trimethylsilyl, triethylsilyl, triisopropylsilyl, dimethylisopropylsilyl, diethylisopropylsily, dimethylthexylsilyl, tert.-butyldimethylsilyl, t-butyldiphenylsilyl, tribenzylsilyl, tri-p-xylylsilyl, triphenylsilyl, diphenylmethylsilyl, t-butylmethoxyphenylsilyl); carboxylic esters (formate, benzoylformate, acetate, choroacetate, dichloroacetate, trichloroacetate, trifluoroacetate, methoxyacetate, triphenylmethoxyacetate, phenoxyacetate, p-chlorophenoxyacetate, p-poly-phenylacetate, 3-phenylpropionate, 4-oxopentanoate (Levulinate), 4,4-(ethylenedithio)pentanoate, pivaloate, adamantoate, crotonate, 4-methoxycrotonate, benzoate, p-phenylbenzoate, 2,4,6-trimethyl-benzoate (mesitoate)); carbonates (methyl, 9-fluorenylmethyl, ethyl, 2,2,2-trichloroethyl, 2-(trimethylsilyl) ethyl, 2-(phenylsulfonyl)ethyl, 2-(triphenylphosphonio) ethyl, isobutyl, vinyl, allyl, p-nitrophenyl, benzyl, p-methoxybenzyl, 3,4-dimethoxybenzyl, o-nitrobenzyl, p-nitrobenzyl, S-benzyl thiocarbonate, 4-ethoxy-1-naphthyl, methyl dithiocarbonate); groups with assisted cleavage (2-iodobenzoate, 4-azidobutyrate, 4-niotro-4-methylpentanoate, o-(dibromomethyl)benzoate, 2-formylbenzenesulfonate, 2-(methylthiomethoxy)ethyl carbonate, 4-(methylthiomethoxy)butyrate, 2-(methylthiomethoxymethyl)benzoate); miscellaneous esters (2,6-di-chloro-4-methylphenoxyacetate, 2,6-dichloro-4-(1,1,3,3 tetramethylbutyl) phenoxyacetate, 2,4-bis(1,1-dimethylpropyl) phenoxyacetate, chorodiphenylacetate, isobutyrate, monosuccinoate, (E)-2-methyl-2-butenoate (Tigloate), o-(methoxycarbonyl)benzoate, p-poly-benzoate, α-naphthoate, alkyl N,N,N',N'-tetramethylphosphorodiamidate, N-phenylcarbamate, 2,4-dinitrophenylsulfenate); and sulfonates (methanesulfonate (mesylate), benzylsulfonate, tosylate). If desired, one of the substituents $R^5$ and $R^6$ may be replaced by another substituent, for example in order to place a substituent with a desired reactivity at the respective position. As an illustrative example, Chen & Du (*Carbohydrate Research* (2007) 342, 1405-1411) have described exchanging a (tert-butyldimethyl)silyl group as $R^6$ for H and for a methyl group.

In some embodiments $R^5$ and $R^6$ hydroxyl protecting groups include substituted methyl ethers, substituted benzyl ethers, silyl ethers, and esters including sulfonic acid esters, such as trialkylsilyl ethers, tosylates, mesylates and acetates.

3,4-Dihydropyran compound (9) may for example be obtained from pentenopyranoside (20)

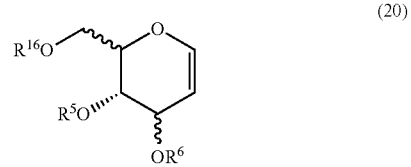

(20)

In pentenopyranoside (20) group $R^{16}$ is a hydroxyl protecting group (see above) that is independently selected from $R^5$ and $R^6$. The symbol ∼∼∼ again, as throughout the entire specification, indicates that the respective bond may have any configuration (see above). The conversion of pentenopyranoside (20), which can be obtained from the respective glucal, galactal or idal (Du, Y., et al., *J. Org. Chem.* (2006) 71, 8446-8451), to 3,4-dihydropyran compound (9), which may e.g. be an arabino-dienitol compound, may for example be carried out as described by Du et al. (ibid.). In some of these as well as in other embodiments 3,4-dihydropyran compound (9) may be of general formula (9A)

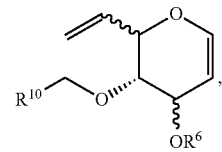

including e.g.

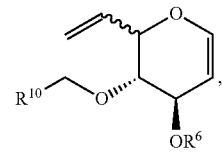

In embodiments of 3,4-dihydropyran compound (9) where this compound can be represented by formula (9A), $R^{10}$ is an aliphatic, alicyclic, aromatic, arylaliphatic, or arylalicyclic group, which may include 0 to about 3 heteroatoms selected from the group N, O, S, Se and Si. In such embodiments $R^5$ consists of a methylene linker and the moiety $R^{10}$. The methylene linker connects moiety $R^{10}$ to the 4-hydroxy group of 3,4-dihydropyran compound (9).

In some embodiments 3,4-dihydropyran compound (9A) is obtained by reacting acetal (7)

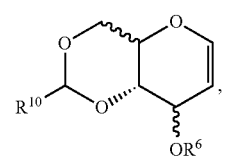

which may e.g. be

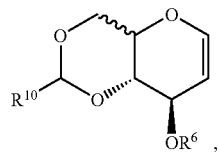

to form 3,4-dihydropyran compound (8)

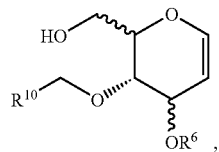

including e.g.

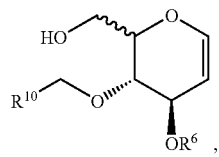

and removing the hydroxy group of 3,4-dihydropyran compound (8) to form 3,4-dihydropyran compound (9A).

In some embodiments a 3,4-dihydropyran compound (8) is obtained from acetal (7) by a cleavage-acetylation, which may be carried out in a one-pot synthesis as described by Agnihotri & Misra (*Tetrahedron Letters* (2006) 47, 3653-3658). A corresponding reaction may be represented by:

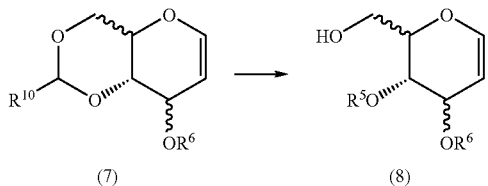

In such embodiments, in 3,4-dihydropyran compound (8) group $R^{10}$ may also be H or be identical to the group $R^{10}$ of acetal (7). A respective methylene linker as in acetal (7) need not be present in 3,4-dihydropyran compound (8). Accordingly a desired group $R^5$ may be introduced into the 3,4-dihydropyran compound (8) at this stage.

Acetal (7) may be obtained by reacting 3,4-dihydropyran compound (5)

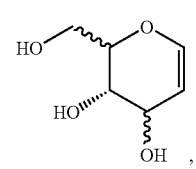

such as e.g.

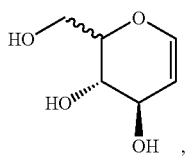

to form acetal (6)

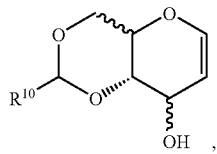

including e.g.

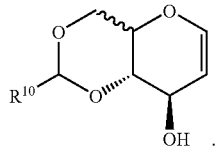

Any suitable acetalisation reaction known in the art may be used. Suitable examples are the reaction with an alkyl-, alkenyl- or aryl halide, with a diazoalkane, -alkene or aryl compound, with an ether or an acetal ("transetherification"), with an alkyne. As an illustrative example, the procedure described by Tsunoda et al. (*Tetrahedron Letters* (1980) 21, 1357-1358) may be employed.

In the process of the invention 3,4-dihydropyran compound (9) is reacted to form an aldehyde of general formula (4):

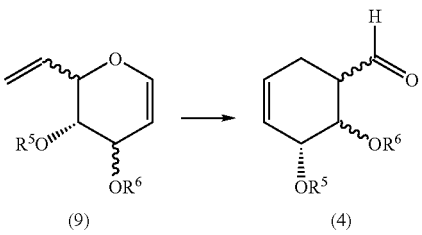

The reaction may for example in some embodiments be represented as follows:

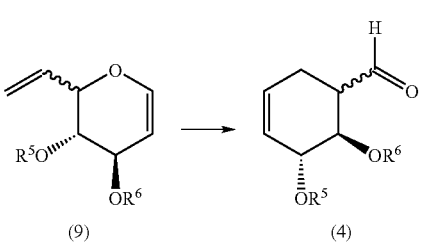

or in some embodiments as follows:

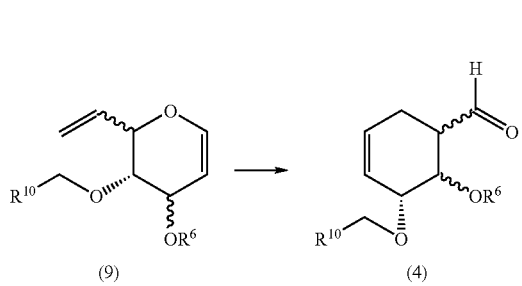

Generally, the reaction is based on a so called Claisen rearrangement. The term "Claisen rearrangement" is accordingly understood under its broader use, referring to a—typically concerted—pericyclic [3,3] sigmatropic rearrangement, rather than merely the rearrangement of an o-allylphenol. This conversion may for instance be carried out by exposing 3,4-dihydropyran compound (9) to an elevated temperature.

Aldehyde (4) is oxidized to carboxylic acid ester (10)

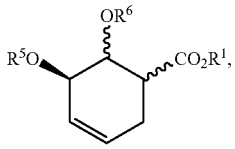

which may in some embodiments be represented by

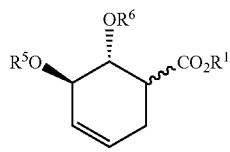

and in some embodiments by

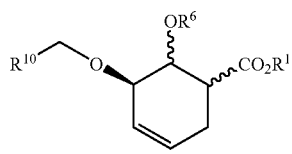

The oxidation may be achieved by contacting aldehyde (4) with an oxidizing agent, which is a compound that gains electrons in a redox reaction. Illustrative examples of a suitable oxidizing agent include, but are not limited to, a chlorite such as sodium chlorite, a hypochlorite, a chlorate, a perchlorate, a permanganate such as potassium permanganate, nitric acid, nitrous oxide, osmium tetroxide, Tollens' reagent (di-amminesilver(I)), a copper(II) salt, ammonium cerium(IV) nitrate, chromium(VI) oxide, a chromate, a dichromate and pyridinium chloro-chromate.

In some embodiments forming carboxylic acid ester (10) includes forming a carboxylic acid (10A):

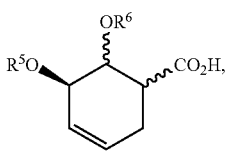

which may in some embodiments also be represented by

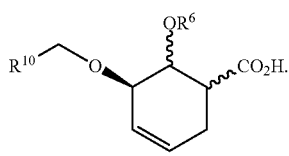

and in some embodiments by

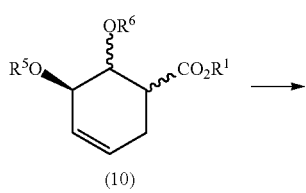

Carboxylic acid (10A) may be converted to carboxylic acid ester (10) by any means including a standard esterification reaction well established in the art.

In the process of the invention carboxylic acid ester (10) is reacted to form N-substituted carbamate (3):

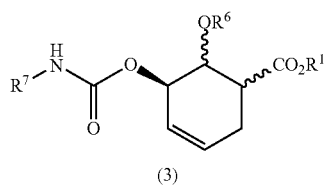

The reaction may for example in some embodiments be represented as follows:

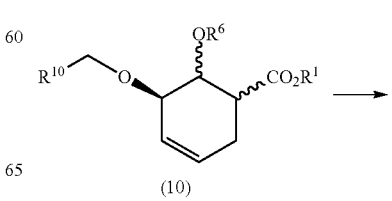

-continued

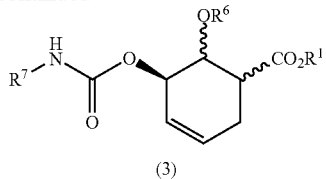

(3)

or in some embodiments as follows:

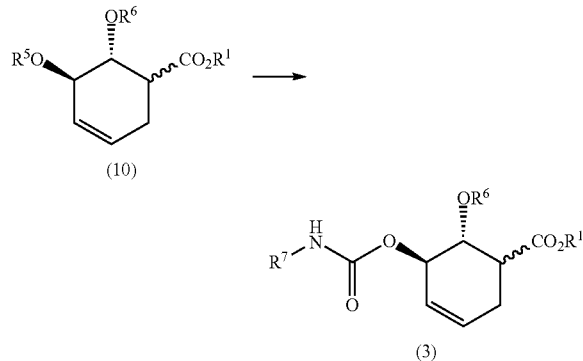

Generally, in this reaction protecting group $R^5$ of carboxylic acid ester (10) is replaced by an N-substituted carbamoyl group. $R^5$ is a suitable amino protecting group. In typical embodiments the amino protecting group $R^5$ (as well as amino protecting groups $R^3$ and $R^4$, see below) is connected to the nitrogen atom of the amino group via a carbon or a silicon atom (which is part of the respective group). A silyl group may be of the structure described above for a silyl ester, i.e. include groups $R^{13}$-$R^{15}$ (supra). Examples of a suitable amino protecting group include, but are not limited to, carbamates (methyl and ethyl, 9-fluorenylmethyl, 9(2-sulfo)fluoroenylmethyl, 9-(2,7-dibromo)fluorenylmethyl, 2,7-di-tert.-buthyl-[9-(10,10-dioxo-10,10,10,10-tetrahydrothioxanthyl)]methyl, 4-methoxyphenacyl); substituted ethyl (2,2,2-trichoroethyl, 2-trimethylsilylethyl, 2-phenylethyl, 1-(1-adamantyl)-1-methylethyl, 1,1-dimethyl-2-haloethyl, 1,1-dimethyl-2,2-dibromoethyl, 1,1-dimethyl-2,2,2-trichloroethyl, 1-methyl-1-(4-biphenyl)ethyl, 1-(3,5-di-tert-butylphenyl)-1-methylethyl, 2-(2'- and 4'-pyridyl)ethyl, 2-(N,N-dicyclohexylcarboxamido)ethyl, tert.-butyl, 1-adamantyl, vinyl, allyl, 1-isopropylallyl, cinnamyl, 4-nitrocinnamyl, 8-quinolyl, N-hydroxypiperidinyl, alkyldithio, benzyl, p-methoxy-benzyl, p-nitrobenzyl, p-bromobenzyl, p-chorobenzyl, 2,4-dichlorobenzyl, 4-methylsulfinyl-benzyl, 9-anthrylmethyl, diphenylmethyl); groups with assisted cleavage (2-methylthioethyl, 2-methylsulfonylethyl, 2-(p-toluenesulfonyl)ethyl, [2-(1,3-dithianyl)methyl, 4-methylthiophenyl, 2,4-dimethylthiophenyl, 2-phosphonioethyl, 2-triphenylphosphornioisopropyl, 1,1-dimethyl-2-cyanoethyl, m-choro-p-acyloxybenzyl, p-(dihydroxyboryl)benzyl, 5-benzisoxazolylmethyl, 2-(trifluoromethyl)-6-chromonylmethyl); groups capable of photolytic cleavage (m-nitrophenyl, 3,5-dimethoxybenzyl, o-nitrobenzyl, 3,4-dimethoxy-6-nitrobenzyl, phenyl(o-nitro-phenyl)methyl); urea-type derivatives (phenothiazinyl-(10)-carbonyl, N'-p-toluenesulfonyl-aminocarbonyl, N'-phenylaminothiocarbonyl); miscellaneous carbamates (t-amyl, S-benzyl thiocarbamate, p-cyanobenzyl, cyclobutyl, cyclohexyl, cyclopentyl, cyclopropylmethyl, p-decyloxybenzyl, diisopropylmethyl, 2,2-dimethoxycarbonylvinyl, o-(N,N-dimethylcarboxamido)benzyl, 1,1-dimethyl-3-(N,N-dimethylcarboxamido)propyl, 1,1-dimethylpropynyl, di(2-pyridyl)methyl, 2-furanylmethyl, 2-Iodoethyl, isobornyl, isobutyl, isonicotinyl, p-(p'-methoxyphenylazo)benzyl, 1-methylcyclobutyl, 1-methylcyclohexyl, 1-methyl-1-cyclopropylmethyl, 1-methyl-1-(3,5-dimethoxyphenyl)ethyl, 1-methyl-1-(p-phenylazophenyl)ethyl, 1-methyl-1-phenylethyl, 1-methyl-1-(4-pyridyl)ethyl, phenyl, p-(phenylazo)benzyl, 2,4,6-tri-t-butylphenyl, 4-(trimethylammonium)benzyl, 2,4,6-trimethylbenzyl); amides (N-formyl, N-acetyl, N-choroacetyl, N-trichoroacetyl, N-trifluoroacetyl, N-phenylacetyl, N-3-phenylpropionyl, N-picolinoyl, N-3-pyridylcarboxamide, N-benzoylphenylalanyl, N-benzoyl, N-p-phenyl-benzoyl); amides with assisted cleavage (N-o-nitrophenylacetyl, N-o-nitrophenoxyacetyl, N-acetoacetyl, (N'-dithiobenzyloxycarbonylamino)acetyl, N-3-(p-hydroxyphenyl)propionyl, N-3-(o-nitrophenyl)propionyl, N-2-methyl-2-(o-nitrophenoxy)propionyl, N-2-methyl-2-(o-phenylazophenoxy)propionyl, N-4-chlorobutyryl, N-3-methyl-3-nitrobutyryl, N-o-nitrocinnamoyl, N-acetylmethionine, N-o-nitrobenzoyl, N-o-(benzoyloxymethyl)benzoyl, 4,5-diphenyl-3-oxazolin-2-one); cyclic imide derivatives (N-phthalimide, N-dithiasuccinoyl, N-2,3-diphenylmaleoyl, N-2,5-dimethylpyrrolyl, N-1,1,4,4-tetramethyldisilylazacyclopentane adduct, 5-substituted 1,3-dimethyl-1,3,5-triazacyclohexan-2-one, 5-substituted 1,3-dibenzyl-1,3-5-triaza-cyclohexan-2-one, 1-substituted 3,5-dinitro-4-pyridonyl); N-alkyl and N-aryl amines (N-methyl, N-allyl, N-[2-(trimethylsilyl)ethoxy]methyl, N-3-acetoxypropyl, N-(1-isopropyl-4-nitro-2-oxo-3-pyrrolin-3-yl), quaternary ammonium salts, N-benzyl, N-di(4-methoxyphenyl)methyl, N-5-dibenzosuberyl, N-triphenylmethyl, N-(4-methoxyphenyl)diphenylmethyl, N-9-phenyl-fluorenyl, N-2,7-dichloro-9-fluorenylmethylene, N-ferrocenylmethyl, N-2-picolylamine N'-oxide), imine derivatives (e.g. N-1,1-dimethylthiomethylene, N-benzylidene, N-p-methoxy-benzylidene, N-diphenylmethylene, N-[(2-pyridyl)mesityl]methylene, N,(N',N'-dimethylaminomethylene, N,N'-isopropylidene, N-p-nitrobenzylidene, N-salicylidene, N-5-chlorosalicylidene, N-(5-chloro-2-hydroxyphenyl)phenylmethylene, N-cyclohexylidene); enamine derivatives (N-(5,5-dimethyl-3-oxo-1-cyclohexenyl)); N-metal derivatives (N-borane derivatives, N-diphenylborinic acid derivatives, N-[phenyl(pentacarbonylchromium- or -tungsten)]carbenzyl, N-copper or N-zinc chelate); N—N derivatives (N-nitro, N-nitroso, N-oxide); N—P derivatives (N-diphenylphosphinyl, N-dimethylthiophosphinyl, N-diphenylthiophosphinyl, N-dialkyl phosphoryl, N-dibenzyl phosphoryl, N-diphenyl phosphoryl); N—Si derivatives; N—S derivatives; N-sulfenyl derivatives (N-benzenesulfenyl, N-o-nitrobenzenesulfenyl, N-2,4-dinitrobenzene-sulfenyl, N-pentachlorobenzenesulfenyl, N-2-nitro-4-methoxybenzenesulfenyl, N-triphenylmethylsulfenyl, N-3-nitropyridinesulfenyl); and N-sulfonyl derivatives (N-p-toluenesulfonyl, N-benzenesulfonyl, N-2,3,6-trimethyl-4-methoxybenzenesulfonyl, N-2,4,6-trimethoxybenzenesulfonyl, N-2,6-dimethyl-4-methoxybenzenesulfonyl, N-pentamethylbenzenesulfonyl, N-2,3,5,6,-tetramethyl-4-methoxybenzenesulfonyl, N-4-methoxybenzene-sulfonyl, N-2,4,6-trimethylbenzenesulfonyl, N-2,6-dimethoxy-4-methylbenzenesulfonyl, N-2,2,5,7,8-pentamethylchroman-6-sulfonyl, N-methanesulfonyl, N-(3-trimethylsilyethanesulfonyl, N-9-anthracenesulfonyl, N-4-(4',8'-dimethoxynaphthylmethyl)benzenesulfonyl, N-benzylsulfonyl, N-trifluoromethylsulfonyl, and N-phenacylsulfonyl).

In some embodiments forming N-substituted carbamate (3) from carboxylic acid ester (10) includes forming hydroxy carboxylic acid (11):

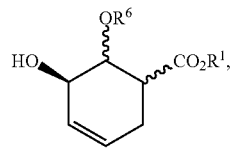

(11)

such as e.g.

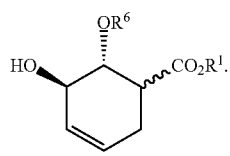

Removing group $R^5$ from carboxylic acid ester (10) in the presence of group $R^6$ may be carried out according to any suitable protocol. For this purpose it may be desired to select the two groups $R^5$ and $R^6$ in advance (see also above). As an illustrative example $R^5$ may be selected to be p-methoxy-benzyl-. Removing moiety $R^5$ may in such embodiments for instance be carried out by contacting carboxylic acid ester (10) with cerie ammonium nitrate, 2,3,-dichloro-5,6-dicyano-1,4-benzoquinone (DDQ), $CBr_4$ in methanol, or $NaBH_3(CN)/BF_3 \cdot Et_2O$.

In some embodiments hydroxy carboxylic acid ester (11) is converted to N-substituted carbamate (3) by contacting hydroxy carboxylic acid ester (11) with 1,1'-carbonyldiimidazole (CDI), thereby forming carbamate (3A)

(3A)

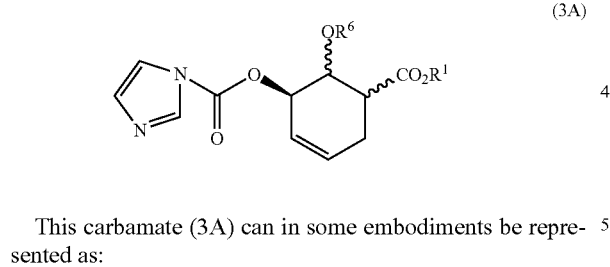

This carbamate (3A) can in some embodiments be represented as:

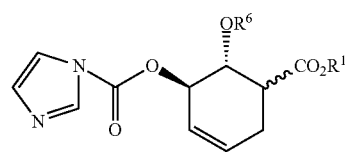

Carbamate (3A) may further be reacted with a compound (15) of general formula $R^7$—X, wherein X is a group selected from halogen, a cyano, an isocyano and a thiocyano group. Thereby N-substituted carbamate (3) is formed.

As a further illustrative example, carbamate (3A) may be converted to N-hydroxycarbamate (17):

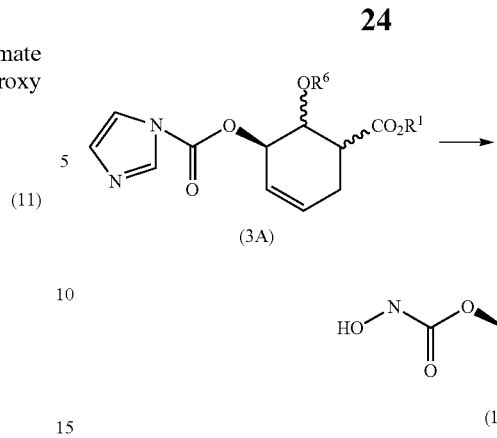

N-hydroxycarbamate (17) may then be converted to N-substituted carbamate (3). A suitable synthesis path in this regard has for example been described by Liu et al. (*J. Org. Chem.* (2007) 72, 5587-5591).

In the process of the invention N-substituted carbamate (3) is reacted to form oxazolinidone (12):

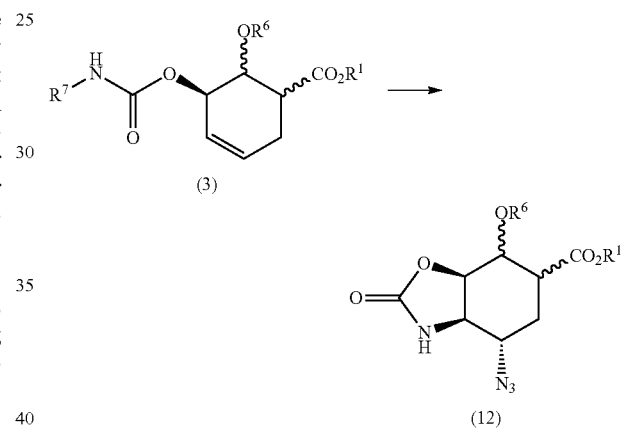

The reaction may for example in some embodiments be represented as follows:

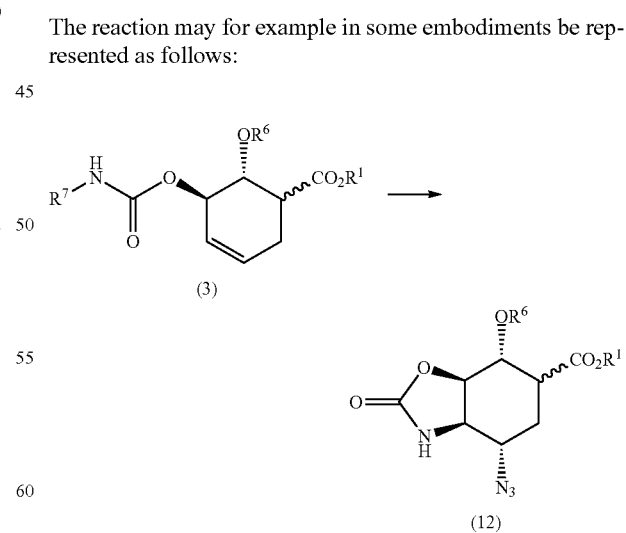

In some embodiments reacting N-substituted carbamate (3) to form oxazolinidone (12) includes contacting N-substituted carbamate (3) with a metal carbonate in the presence of a suitable catalyst such as 1,3-bis(2,6-diisopropylphenyl)imidazolium chloride (Chemical Abstracts No. 250285-32-6). Reacting N-substituted carbamate (3) to form oxazolinidone (12) may further include adding an azido compound under suitable conditions. Any azido compound may be used that is capable of reacting with N-substituted carbamate (3) or an intermediate formed therefrom in the reaction of forming oxazolinidone (12) depicted above. An illustrative example of a suitable azido compound is an azidotrialkylsilane. A respective azido compound may be added together with an organic fluoride salt under suitable conditions.

In some embodiments N-substituted carbamate (3) may be formed via the formation of a bicyclic ring system as described by Liu et al. (supra).

From oxazolinidone (12) the moiety $OR^6$ is removed to form oxazolinidone (13):

(13)

$R^8$ is H or one of a silyl-group, an aliphatic group, an alicyclic group, an aromatic group, an arylaliphatic group, and an arylalicyclic group, which may optionally include 0 to about 3 heteroatoms, such as 0 to about 2 heteroatoms, which may for example be N, O, S, Se or Si. As can be inferred from the structure of product (13), the removal of moiety $OR^6$ may be induced by the removal of substituent $R^6$, which may be followed or accompanied by a removal of the oxygen atom. In some embodiments the formation of oxazolinidone (13) may be carried out via an elimination reaction. Any suitable reagent such as a base may be used in this regard. Accordingly, an agent that is suitable of removing a respective substituent $R^6$ and an agent that is suitable for removing the oxygen atom may be used. In some embodiments one agent may perform both functions. As an illustrative example, where $R^6$ is a silyl group, it may for example be removed using an acid or a fluoride. An agent that is suitable for removing a silyl group and that is at the same time suitable to induce elimination is the mild base tetra-n-butylammonium fluoride.

Typically oxazolinidone (13) has an absolute stereochemistry that can be defined as (3S,4R,5S). Forming oxazolinidone (13) from oxazolinidone (12) may include contacting oxazolinidone (12) with a Brønsted base. Any Brønsted base may be used that is capable of achieving elimination and that leaves oxazolinidone (13) at least to an acceptable amount intact. In some embodiments it may be advantageous to use a bulky base in order to facilitate elimination. Suitable examples include, but are not limited to, a diazabicyclononene such as 1,5-diazabicyclo[4.3.0]non-5-ene, a diazabicycleundecene such as 1,8-diazabicycle[5.4.0]undec-7-ene, a diazabicyclooctane such as 1,4-diazabicyclo[2.2.2]octane, a diisopropylalkylamine such as N,N-diisopropylethylamine, a tetra-alkylguanidine, pyridine, an alkali-alcoholate and an alkali hydride such as sodium hydride.

Thus, in some embodiments the reaction of oxazolinidone (12) in forming oxazolinidone (13) may be represented as:

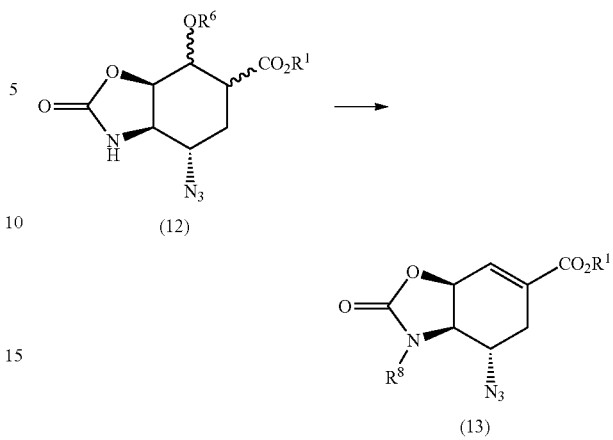

As will be apparent to the skilled artisan, regardless of the stereochemistry of the carboxy containing moiety and the oxy containing moiety (e.g. alkoxy, hydroxy) in the reacting oxazolinidone (12), the product (13) will be of the structure depicted above. Accordingly, in some embodiments the reaction may be represented as:

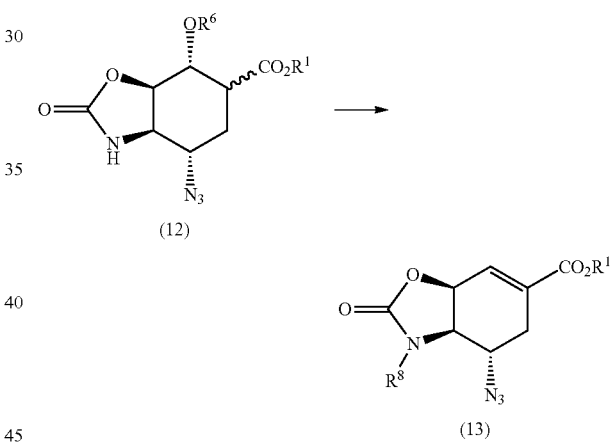

Nevertheless, certain configurations in the reactant (12) may favour the reaction of forming oxazolinidone (13). Further, since $R^6$ is being removed during the present reaction, this moiety may be freely selected upon optimizing the reaction conditions of a desired embodiment.

As indicated above, in some embodiments the formation of oxazolinidone (13) may be represented as:

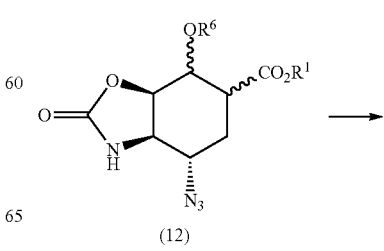

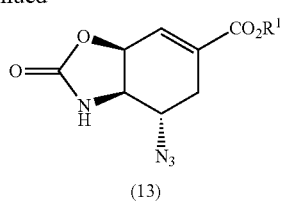

(13)

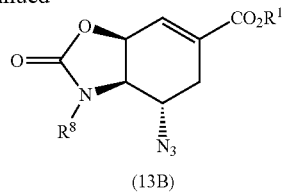

(13B)

However, in some embodiments the moiety $R^8$ (see above) differs from H. Accordingly, during the formation of oxazolinidone (13) a further substituent may be introduced. A substituent at the respective amide nitrogen atom may also be introduced at a later step if desired (see below).

Figure 8:
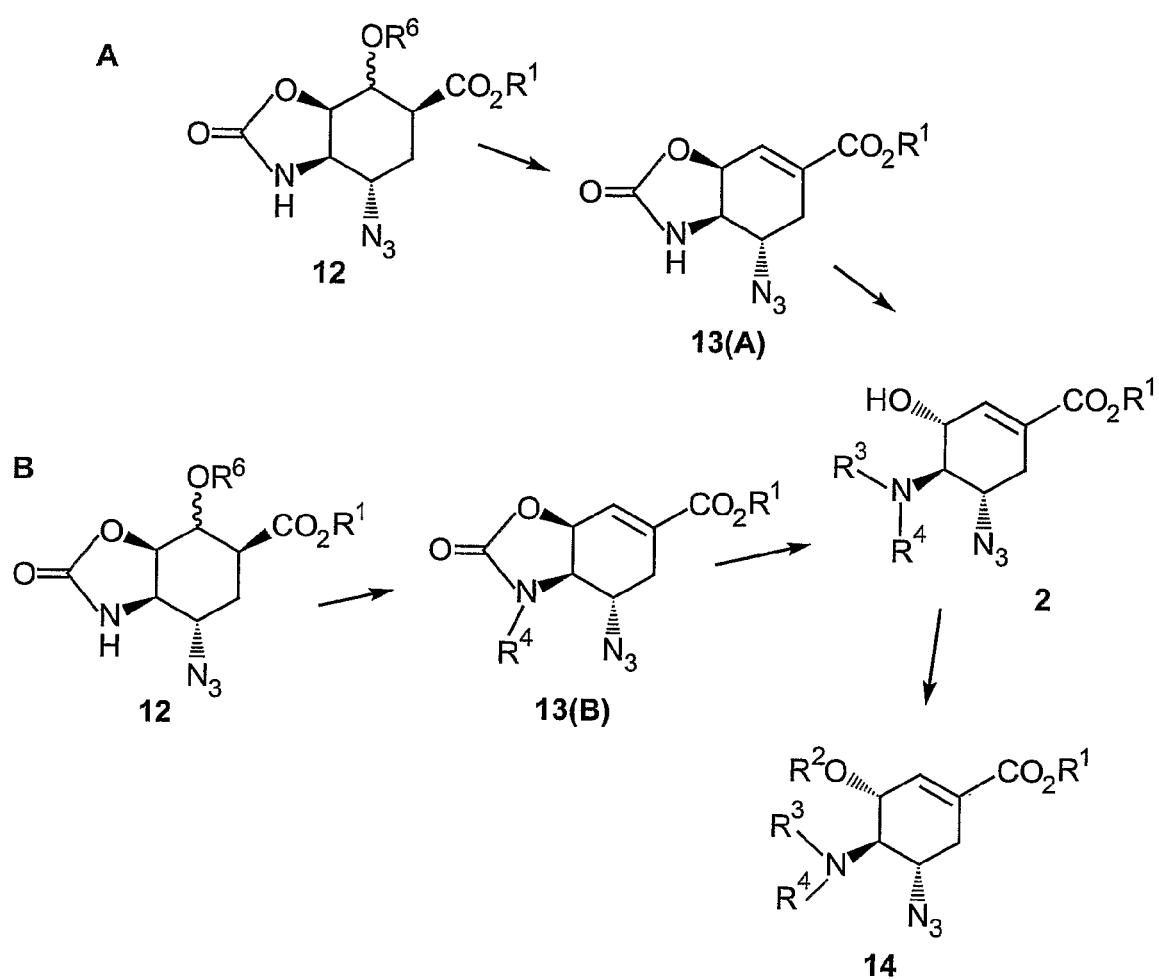
FIG. 8 shows a second route, in two embodiments, of the last three steps depicted in the general synthesis of FIG. 4.

Thus, in some embodiments at the same time a moiety $R^8$ is introduced that differs from H. This moiety may, for instance, be $R^3$ or $R^4$ (see e.g. FIG. 8). Accordingly, in some embodiments the reaction may be represented as:

In other embodiments the process may, at least theoretically, be represented as:

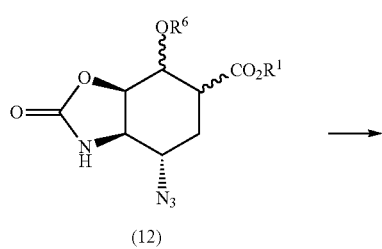

(12)

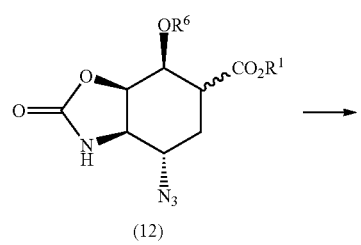

(12)

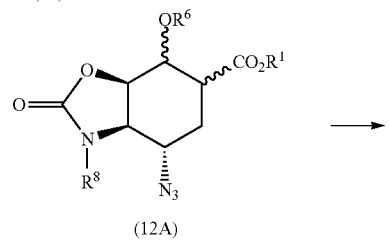

(12A)

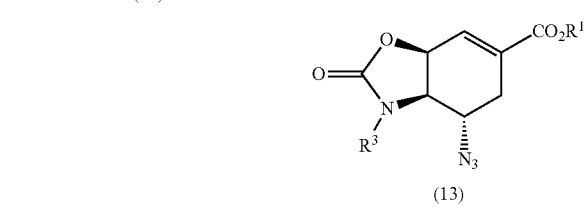

(13)

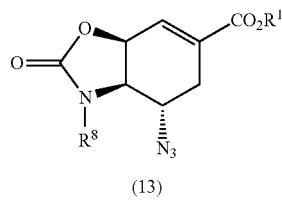

(13)

The process may in some embodiments proceed via an intermediate of oxazolinidone (13) as shown above and thus, at least theoretically be represented as:

Oxazolinidone (13) is reacted to form azido carboxylate ester (2).

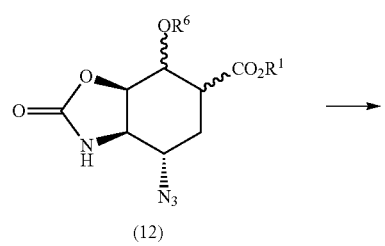

(12)

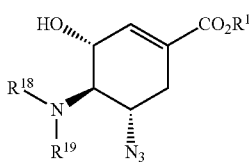

(2)

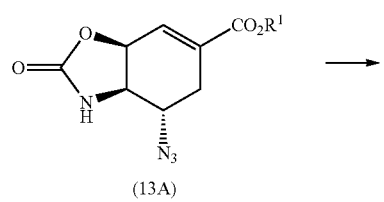

(13A)

In this formula (2) $R^{18}$ and $R^{19}$ are independent from one another H, a silyl-group, an aliphatic, an alicyclic, an aromatic, an arylaliphatic, or an arylalicyclic group. In some embodiments $R^{18}$ is identical to $R^3$ and in some embodiments $R^{19}$ is identical to $R^4$. In some embodiments $R^{18}$ and $R^3$ as well as $R^{19}$ and $R^4$ are identical.

Typically azido carboxylate ester (2) has an absolute stereochemistry that can be defined as (3R,4R,5S). Illustrative examples of azido carboxylate ester (2) are (3R,4R,5S)-4-(acetyl amino)-5-azido-3-hydroxy-1-cyclohexene-1-carboxylic acid ethyl ester (Chemical Abstracts No. 949908-51-4), (3S,4R,5R)-4-(acetylamino)-3-azido-5-hydroxy-1-cyclohexene-1-carboxylic acid phenylmethyl ester (CAS.-Nos 221386-80-7 and 220290-36-8), (3R,4R,5S)-4-

(acetylamino)-5-azido-3-hydroxy-1-cyclohexene-1-carboxylic acid methyl ester (CAS.-No. 208720-48-3). Reacting oxazolinidone (13) to form azido carboxylate ester (2) may in some embodiments include contacting oxazolinidone (13) with a molecule of general formula $R^3$-A-$R^3$ under suitable conditions. In this formula A may be O, S, Se, P or N. As noted above, in some embodiments $R^3$ is an acyl group. In some of these embodiments the molecule of general formula $R^3$-A-$R^3$ is a carboxylic acid anhydride. The group $R^4$ may be introduced in the same way if $R^4$ differs from H. In some embodiments the group $R^4$ may for example be introduced by means of an alkyl halide, a diazo compound or any other method known in the art.

In some embodiments reacting oxazolinidone (13) to form azido carboxylate ester (2) includes forming an azido carboxylate ester of general formula (19)

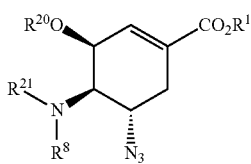

(19)

In this formula (19) $R^{20}$ and $R^{21}$ are independent from one another H, a silyl-group, an aliphatic group, an alicyclic group, an aromatic group, an arylaliphatic group, or an arylalicyclic group. In some embodiments $R^{21}$ is identical to $R^3$ and in some embodiments $R^8$ is identical to $R^4$. In some embodiments $R^{21}$ and $R^3$ as well as $R^8$ and $R^4$ are identical. Azido carboxylate ester (19) may then be further converted to azido carboxylate ester (2). In some embodiments converting azido carboxylate ester (19) to azido carboxylate ester (2) may be carried out via forming an azido carboxylate ester (21)

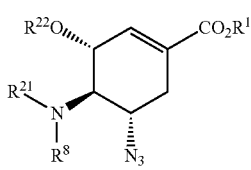

(21)

In this formula $R^{22}$ may be H, a silyl-group, an aliphatic group, an alicyclic group, an aromatic group, an arylaliphatic group or an arylalicyclic group. In some embodiments $R^{22}$ is identical to $R^{20}$. Azido carboxylate ester (21) may then, i.e. in embodiments where it is formed, conveniently be converted to azido carboxylate ester (2) by removing substituent $R^{22}$. It may in some embodiments also be converted to aziridino carboxylate ester (16) in a manner as described for azido carboxylate ester (2) below.

Azido carboxylate ester (2) is converted to 4,5-diamino cyclohexene carboxylate ester (1). The reaction may for example be carried out as described by Shie et al. (2007, supra), i.e. using 2,2,2-trichloro-ethanimidic acid 1-ethylpropyl ester and trifluoromethane-sulfonic acid. In some embodiments azido carboxylate ester (2) is reacted to form azido carboxylate ester (14)

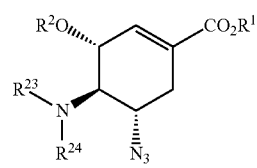

(14)

In this formula (14) the substituents $R^{23}$ and $R^{24}$ are independent from one another H, a silyl-group, an aliphatic group, an alicyclic group, an aromatic group, an arylaliphatic group or an arylalicyclic group. In some embodiments $R^{23}$ is identical to $R^{21}$ and in some embodiments $R^{24}$ is identical to $R^8$. In some embodiments $R^{23}$ and $R^{21}$ as well as $R^{24}$ and $R^8$ are identical. In some embodiments $R^{23}$ is identical to $R^3$ and in some embodiments $R^{24}$ is identical to $R^4$.

Examples of an azido carboxylate ester of general formula (14) include, but are not limited to, (3R,4R,5S)-4-(acetylamino)-5-azido-3-methoxy-1-cyclohexene-1-carboxylic acid methyl ester (CAS No 187226-65-9), (3R,4R,5S)-4-(acetylamino)-5-azido-3-propoxy-1-cyclohexene-1-carboxylic acid methyl ester (CAS No 187226-65-9), (3R,4R,5S)-4-(acetylamino)-5-azido-3-[(1R)-1-methylpropoxy]-1-cyclohexene-1-carboxylic acid methyl ester (CAS No 187226-74-0), (3R,4R,5S)-4-(acetylamino)-5-azido-3-(1-propylbutoxy)-1-cyclohexene-1-carboxylic acid methyl ester (CAS No 187226-81-9), (3R,4R,5S)-4-(acetylamino)-5-azido-3-(2-propen-1-yloxy)-1-cyclohexene-1-carboxylic acid methyl ester (CAS No 208720-33-6), (3R,4R, 5S)-4-(acetylamino)-5-azido-3-(1-ethylpropoxy)-1-cyclohexene-1-carboxylic acid ethyl ester (CAS No 204255-06-1), (3S,4R,5R)-4-(acetylamino)-5-(acetyloxy)-3-azido-1-cyclohexene-1-carboxylic acid diphenylmethyl ester (CAS No 208720-39-2), N-[(1,1-dimethylethoxy)carbonyl]-glycine (1R,5S,6R)-6-(acetylamino)-5-azido-3-[(diphenylmethoxy)carbonyl]-3-cyclohexen-1-yl ester (CAS No 208720-40-5), (3R,4R,5S)-4-(acetylamino)-5-azido-3-(1,1-dimethyl-propoxy)-1-cyclohexene-1-carboxylic acid methyl ester (CAS No 208720-72-3), N-[(1,1-dimethylethoxy)carbonyl]-glycine (1R,5S,6R)-6-(acetylamino)-5-azido-3-[(phenylmethoxy)carbonyl]-3-cyclohexen-1-yl ester (CAS No 221386-82-9), (3R,4R,5S)-4-(acetylamino)-5-azido-3-(2-hydroxypropoxy)-1-cyclohexene-1-carboxylic acid methyl ester (CAS No 221386-64-7), (3R,4R,5S)-4-(acetylamino)-3-[2-(acetyloxy)ethoxy]-5-azido-1-cyclohexene-1-carboxylic acid methyl ester (CAS No 221386-85-2), (3R,4R,5S)-4-(acetylamino)-5-azido-3-[(1R)-1-ethyl-3-phenylpropoxy]-1-cyclohexene-1-carboxylic acidmethyl ester (CAS No 221387-40-2), (3R,4R,5S)-4-(acetylamino)-5-azido-3-[(1R)-1-ethyl-3-oxopropoxy]-1-cyclohexene-1-carboxylic acid ethyl ester (CAS No 252191-23-4), (3R,4R,5S)-4-(acetylamino)-5-azido-3-[(ethoxycarbonyl)oxy]-1-cyclohexene-1-carboxylic acid ethyl ester (CAS No 289669-84-7) and (3R,4R,5S)-4-(acetylamino)-3-(acetyloxy)-5-azido-1-cyclohexene-1-carboxylic acid methyl ester (CAS No 518003-69-5).

In some embodiments reacting azido carboxylate ester (2) to form 4,5-diamino cyclohexene carboxylate ester (1) includes forming a 5-azido-7-azabicyclo[4.1.0]hept-2-ene-3-carboxylic acid ester of general formula (16):

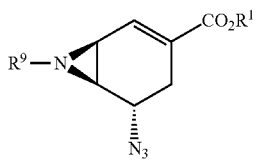

(16)

In azabicyclo compound (16) the substituent $R^9$ may be a silyl-group, an aliphatic, an alicyclic, an aromatic, an arylaliphatic or an arylalicyclic group.

Figure 7:
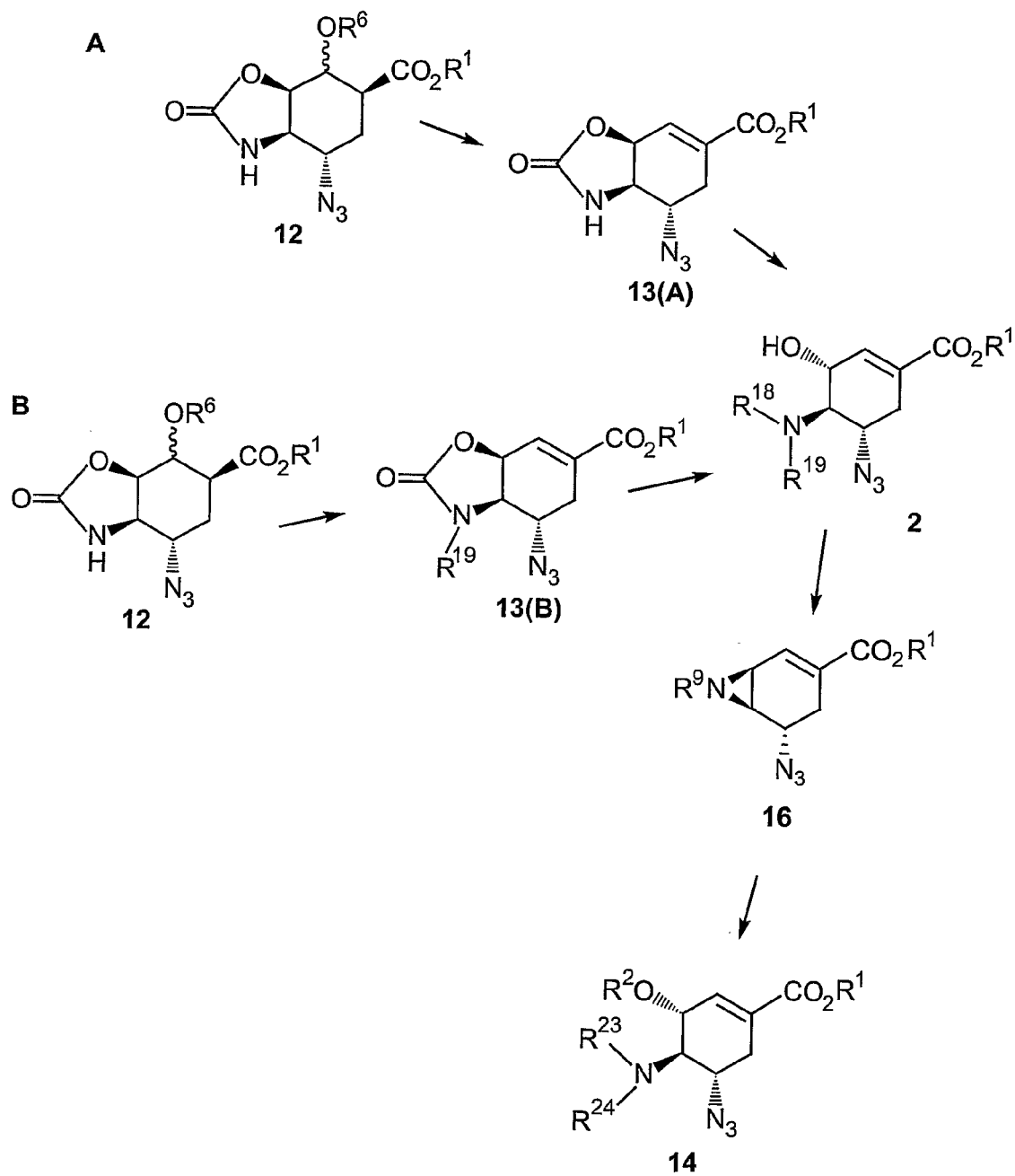
FIG. 7 shows a first route, in two embodiments, of the last three steps depicted in the general synthesis of FIG. 4.

In some embodiments reacting azido carboxylate ester (2) to form azabicyclo compound (16) is included in the synthesis of azido carboxylate ester (14), as for instance illustrated in FIG. 7. In such embodiments azabicyclo compound (16) may be directly converted to azido carboxylate ester (14), for example by adding an alcohol. The corresponding alcohol may introduce the moiety —$OR^2$ into the molecule. One or more subsequent reactions may then be required to introduce substituents $R^3$ and $R^4$ into the molecule.

In some reactions within a process according to the present invention a functional group is introduced into the molecule of interest. An example is the conversion of azabicyclo compound (16) to azido carboxylate ester (14). In such cases the reactant, which may be considered the first reactant used may be a molecule that forms a covalent link with a precursor of the molecule of interest. This precursor, which has been formed in a previous reaction of the process of the invention, e.g. compound 16, may be termed a second reactant molecule. The formation of this covalent bond may be achieved via the reaction of a functional group of the first reactant molecule. Thereby a moiety such as $R^2$ may be introduced into the molecule of interest. As explained above, such a moiety may include one or more functional groups. Accordingly, the first reactant molecule may also contain one or more additional functional groups.

Such additional functional groups may have a much lower reactivity under the respective reaction conditions than the functional group that forms a covalent link with a precursor of the molecule of interest. As an illustrative example, halogen or CHO-substituents in an ortho- or para position to a hydroxyl group on an aromatic ring generally possess a much lower reactivity than the functional group that forms a covalent link with a precursor of the molecule of interest. Additional functional groups with a reactivity comparable to the functional group that forms a covalent link with a precursor of the molecule of interest may however as such give rise to undesired side reactions. Thereby the overall yield of the process of the invention may be reduced. Nevertheless, if reactants with such additional functional groups are desired to be used in the present invention, this can be achieved by the use of protecting groups, which is a well established method in the art (see also above). Using this approach, the additional functional groups are shielded from participating in the reaction. A large number of protecting groups, which are well known to those skilled in the art, is available for various functional groups. As an example, carboxylic groups as nucleophiles may be protected by converting them into an ester, while hydroxyl groups may for instance be protected by an isopropylidene group. Such protecting groups may be removed after the reaction has been carried out. For example, the isopropylidene protecting group shielding a hydroxyl group may be removed by acid treatment. Those skilled in the art will furthermore be aware that such protecting groups may have to be introduced well in advance during the synthesis of the respective reactant.

Azido carboxylate ester (14) can be converted to 4,5-diamino cyclohexene carboxylate ester (1). Any reduction reaction known in the art may for instance be used to convert the 5-azido group into an amino group. In embodiments where $R^{11}$ is H and $R^{12}$ is —C(=NH)—$NH_2$, a thiourea derivative may be used to introduce this group, as described by Shie et al. (2007, supra).

The conditions, including solvents used in the individual reactions of the process of the invention may be selected according to the corresponding reaction. It is within the knowledge of the person skilled in the art to choose and optimize the solvents and reaction conditions, starting for instance from standard protocols known in the art. Suitable solvents that may be used in the reactions of the present invention include solvents that are nonreactive under the selected reaction conditions as well as solvents that are reactive under the selected reaction conditions. Nevertheless, the pure fact that certain solvents may themselves be able to react with a reactant molecule formed in the previous reaction of the process, may be taken into consideration for the selection of the solvent. In some embodiments it may be sufficient to choose solvents with a lower reactivity than the reactants used. It may for example be sufficient to use a solvent of a lower nucleophilicity than a nucleophilic compound selected as a reactant.

The synthetic route of the present invention is highly practical, efficient and straightforward to culminate in a stereoselective synthesis of a 4,5-diamino cyclohexene carboxylate ester or a pharmaceutically acceptable salt thereof, such as oseltimivir phosphate. All the transformations in the synthesis proceed in high yields. Some intermediates are straightly carried over to the next step without purification, and some other intermediates can be crystallized without column chromatographic processes. Inexpensive and commonly used reagents are used in the synthesis of the invention, in particular a monosaccharide such as glucose as the starting material. The synthetic scheme also allows late-stage functionalization, which keeps the door open to many 4,5-diamino cyclohexene carboxylate esters and derivatives thereof, e.g. oseltimivir analogues.

In order that the invention may be readily understood and put into practical effect, particular embodiments will now be described by way of the following non-limiting examples.

EXAMPLES

To a solution of D-(+)-glucal (10.0 g, 68 mmol) and p-anisaldehyde dimethylacetal (20 mL, 102 mmol) in dry DMF (150 mL), 0.86 g (3.4 mmol) of PPTS was added. The mixture was stirred at room temperature under reduced pressure to remove generated ethanol for 3 h. The reaction mixture was then cooled to room temperature. Solvent was removed and the residue was dissolved in $CH_2Cl_2$. The solution was washed with saturated aqueous $NH_4Cl$, $H_2O$, and brine. The organic layer was dried over $Na_2SO_4$, filtered, and then concentrated in vacuo. The residue was purified by flash column chromatography on silica gel (EtOAc/hexane=1:2) to afford 4,6-Di-O-(4-methoxybenzylidene)-D-(−)-glucal (compound 6, 14 g, 78%) as a white solid.

$^1$H NMR (CDCl$_3$, 400 MHz): δ 7.42 (d, J=8.7 Hz, 2H), 6.90 (d, J=8.7 Hz, 2H), 6.34 (dd, $J_{1,2}$=6.1 Hz, $J_{1,3}$=1.3 Hz, 1H), 5.55 (s, 1H), 4.77 (dd, $J_{1,2}$=6.1 Hz, $J_{2,3}$=1.9 Hz, 1H), 4.50-4.47 (m, 1H), 4.36 (dd, $J_{1,2}$=10.3 Hz, $J_{1,3}$=5 Hz, 1H), 3.80 (s, 3H), 3.93-3.75 (m, 3H), 2.44 (d, J=4.2 Hz, 1H); $^{13}$C NMR (CDCl$_3$, 100 MHz): 6160.2, 144.1, 129.5, 127.5, 113.7, 103.5, 101.7, 80.6, 68.3, 68.2, 66.5, 55.3. HRMS (ESI) calcd for $C_{14}H_{16}O_5Na$ [M+Na$^+$]: 287.0895, found: 287.0888.

To a solution of 4,6-Di-O-(4-methoxybenzylidene)-D-(−)-glucal (compound 6, 7.7 g, 29.1 mmol) in DMF (40 mL), there were added imidazole (3.96 g, 58.2 mmol), TBDMSCl (5.26 g, 34.9 mmol) and a catalytic amount of DMAP at rt under nitrogen atmosphere. After 3 h at room temperature, the reaction mixture was diluted with $CH_2Cl_2$, washed with saturated $NH_4Cl$ solution and dried over $Na_2SO_4$. Evaporation of the organic solvent under reduced pressure gave a crude product, which was purified by flash column chromatography on silica gel (EtOAc/hexane=1:15) to afford 3-tert-butyldimethylsilyl-4,6-Di-O-(4-methoxybenzylidene)-D-(−)-glucal (compound 7, 10 g, 90%) as a colorless oil.

IR (neat) $v_{max}$=2932, 2858, 1640, 1520, 1249, 1103, 868 cm$^{-1}$; $^1$H NMR (CDCl$_3$, 400 MHz): δ 7.42 (d, J=8.7 Hz, 2H), 6.89 (d, J=8.7 Hz, 2H), 6.29 (dd, $J_{1,2}$=6.1 Hz, $J_{1,3}$=1.4 Hz, 1H), 5.56 (s, 1H), 4.67 (dd, $J_{1,2}$=6.1 Hz, $J_{1,3}$=1.9 Hz, 1H), 4.51-4.49 (m, 1H), 4.35-4.31 (m, 1H), 3.88-3.76 (m, 6H), 0.90 (s, 9H), 0.10-0.08 (d, 6H); $^{13}$C NMR (CDCl$_3$, 100 MHz): δ 159.9, 143.3, 129.9, 127.3, 113.5, 105.4, 101.2, 80.5, 68.8, 68.3, 67.3, 55.2, 25.8, 18.2, −4.4, −4.8; HR/MS (ESI) calcd for $C_{14}H_{16}O_5$ [M+H$^+$], 379.1941, found 379.1938.

To a solution of 3-tert-butyldimethylsilyl-4,6-Di-O-(4-methoxybenzylidene)-D-O-glucal (compound 7, 10.0 g, 26.4 mmol) in freshly distilled $CH_2Cl_2$ (50 mL), DIBAL-H (1M in toluene, 31.7 mL, 31.7 mmol) was slowly added at −15° C. under nitrogen. The reaction mixture was stirred at −15° C. for 20 min and at rt for 2 h, then it was cooled to 0° C. and MeOH (1 mL) was added dropwise. EtOAc (30 mL) and sodium potassium tartrate (20%-$H_2O$, 30 mL) were added at room temperature. The mixture was stirred for 1 h, extracted with EtOAc (2×30 mL). The organic layers were washed with brine (2×50 mL) and dried over $Na_2SO_4$. Filtration and evaporation of the solvent under reduced pressure gave a crude product, which was purified by flash column chromatography on silica gel (EtOAc/hexane=1:3) to afford 8 (7.6 g, 84%) as colorless oil.

$^1$H NMR (CDCl$_3$, 400 MHz): δ 7.28 (d, J=8.6 Hz, 2H), 6.88 (d, J=8.6 Hz, 2H), 6.33 (d, $J_{1,2}$=6.0 Hz, 1H), 4.77 (d, J=11 Hz, 1H), 4.67 (dd, $J_{1,2}$=4.9 Hz, $J_{2,3}$=2.9 Hz 1H), 4.63 (d, J=11 Hz, 1H), 4.35-4.33 (m, 1H), 3.96-3.92 (m, 1H), 3.82-3.80 (m, 5H), 3.63-3.60 (m, 1H), 2.10 (t, J=6.6 Hz 1H), 0.92 (s, 9H), 0.12 (s, 6H); $^{13}$C NMR (CDCl$_3$, 100 MHz): δ 159.9, 143.3, 130.0, 129.6, 113.9, 103.4, 76.4, 73.5, 68.6, 55.3, 25.8, 18.0, −4.4, −4.7; HR/MS (ESI) calculated for $C_{20}H_{32}O_5SiNa$ [M+Na$^+$], 403.1917, found 403.1902.

Dess-Martin periodinate (17 g, 40 mmol) was added to a solution of 3,4-dihydropyran compound (8) (7.6 g, 20 mmol) in dry $CH_2Cl_2$ (120 mL). The suspension was stirred for 2 h at room temperature under nitrogen. Saturated aqueous $Na_2S_2O_3$ (50 mL) and $NaHCO_3$ (50 mL) were added slowly to the reaction mixture. The resulting solution was separated. The organic layer was washed with saturated $NaHCO_3$ solution and brine, dried over $Na_2SO_4$, filtered through a pad of Celite and silica gel, evaporated to afford crude aldehyde as colorless oil. To a suspension of methyltriphenylphosphonium bromide (9.44 g, 26.4 mmol) in anhydrous THF (60 mL) was added a solution of n-butyl lithium (1.6 M in hexane, 14.9 mL, 23.8 mmol). After the additional completed, the resulting orange solution was stirred at room temperature for 2 h and then cooled to −78° C. Then a solution of aldehyde (5.0 g, 13.2 mmol) in 20 mL anhydrous THF was added via a cannula. The suspension was stirred for 30 min at −78° C. and 1 h at room temperature, after which it was quenched with saturated aqueous ammonium chloride solution and diluted with ethyl acetate. The solution was separated and the aqueous layer was extracted with ethyl acetate. The combined organic layers were washed with water and dried over $Na_2SO_4$. After removing the solvent, the residue was purified by flash chromatography on neutral $Al_2O_3$ (EtOAc/hexane=1:40) to afford the alkene 9 (3.4 g, 60%) as a colorless oil.

$^1$H NMR (CDCl$_3$, 400 MHz): δ 7.26 (d, J=8.6 Hz, 2H), 6.87 (d, J=8.6 Hz, 2H), 6.33 (d, $J_{1,2}$=6.1 Hz, 1H), 6.06-5.97 (m, 1H), 5.42-5.26 (m, 2H), 4.71-4.57 (m, 3H), 4.36-4.34 (m, 1H), 4.28 (t, J=7.6 Hz, 1H), 3.80 (s, 3H), 3.42 (dd, J 1,2=6.2 Hz, $J_{1,3}$=8.6 Hz, 1H), 0.92 (s, 9H), 0.1 (s, 6H); $^{13}$C NMR (CDCl$_3$, 100 MHz): δ 159.3, 143.2, 134.6, 130.2, 129.6, 118.1, 113.7, 103.9, 80.1, 78.1, 73.8, 69.1, 55.3, 25.8, 18.0, −4.4, −4.6; HR/MS (ESI) calculated for $C_{21}H_{32}O_4SiNa$ [M+Na$^+$], 399.1968, found 399.1976.

A solution of 3,4-dihydropyran compound (9) (3.25 g, 8.6 mmol) in diphenyl ether (5 mL) was heated to 210° C. and stirred in a sealed tube filled with nitrogen. After 2 h, the mixture was cooled to room temperature and purified by column chromatography on silica gel (EtOAc/hexane=1:15) to give aldehyde 4 (2.84 g, 88%) as a colorless oil.

$^1$H NMR (CDCl$_3$, 400 MHz): δ 9.72 (s, 1H), 7.24 (d, J=8.6 Hz, 2H), 6.87 (d, J=8.6 Hz, 2H), 5.85-5.69 (m, 2H), 4.49 (dd, $J_{1,2}$=11.3 Hz, $J_{1,3}$=17.6 Hz, 2H), 4.23 (dd, $J_{1,2}$=5.2 Hz, $J_{1,3}$=7.6 Hz, 1H), 3.83-3.80 (m, 4H), 2.71-2.66 (m, 1H), 2.43-2.20 (m, 2H), 0.86 (s, 9H), 0.07 (d, 6H); $^{13}$C NMR (CDCl$_3$, 100 MHz): δ 202.1, 159.1, 130.3, 129.3, 127.9, 125.3, 113.7, 77.3, 70.5, 70.4, 55.2, 52.2, 25.8, 22.2, 18.1, −4.3, −4.9; HR/MS (ESI) calculated for $C_{21}H_{32}O_4SiNa$ [M+Na$^+$], 399.1968, found 399.1957

To a solution of (4) (2.9 g, 7.7 mmol) and 2-methyl-2-butene (4 mL, 38.5 mmol) in t-BuOH/$H_2O$ mixture (60 mL, 5:1 v/v) were added $NaH_2PO_4$ (2.77 g, 23.1 mmol) and sodium chlorite (2.61 g, 80 wt %, 23.1 mmol). The mixture was stirred at room temperature for 2 h. The mixture was partitioned between EtOAc and brine. The aqueous layer was extracted with EtOAc. The combined organic layers were dried over $Na_2SO_4$, filtered, and concentrated in vacuo to give as colorless oil. To a solution of compound obtained above in DMF (30 mL) were added $K_2CO_3$ (1.6 g, 11.55 mmol) and EtI (1.23 mL, 15.4 mmol). The mixture was stirred at room temperature for 3 h. The mixture was partitioned between $Et_2O$ and $H_2O$. The aqueous layer was extracted with $Et_2O$. The combined organic layers were dried over $Na_2SO_4$, filtered, and concentrated. The residue was purified by column chromatography on silica gel (EtOAc/hexane=1:15) give (10) (2.82 g, 87%) as a colorless oil $^1$H NMR (CDCl$_3$, 400 MHz): δ 7.26 (d, J=8.4 Hz, 2H), 6.86 (d, J=8.4 Hz, 2H), 5.75-5.65 (m, 2H), 4.51 (dd, $J_{1,2}$=11.2 Hz, $J_{1,3=21.4}$ Hz, 2H), 4.15-4.06 (m, 3H), 3.90 (s, 1H) 3.80 (s, 3H), 2.79-2.72 (m, 1H), 2.41-2.25 (m, 2H), 1.24 (t, J=7.1 Hz, 3H), 0.84 (s, 9H), 0.05 (d, 6H); $^{13}$C NMR (CDCl$_3$, 100 MHz): δ 173.6, 158.9, 130.6, 129.2, 127.3, 125.5, 113.6, 79.9, 72.1, 70.2, 60.5, 55.2, 47.3, 28.0, 25.8, 18.1, 14.0, −4.0, −5.3; HR/MS (ESI) calculated for $C_{23}H_{36}O_5SiNa$ [M+Na$^+$], 443.2230, found 443.2219.

DDQ (2.36 g, 10.4 mmol) was added to a solution of 10 (2.8 g, 6.9 mmol) in $CH_2Cl_2/H_2O$ (40 mL, 1:1v/v). The mixture was stirred at room temperature. After 6 h, $Na_2S_2O_3$ (40 mL) was added to the mixture. The suspension was filtered. The filtrate was extracted with $CH_2Cl_2$. The organic layer was washed with saturated $NaHCO_3$ solution and brine successively, dried over $Na_2SO_4$, filtered, and evaporated. The residue was purified by column chromatography on silica gel (EtOAc/hexane=1:8) to give 11 (1.8 g, 87%) as colorless oil.

$^1$H NMR (CDCl$_3$, 400 MHz): δ 5.71-5.57 (m, 2H), 4.13 (q, J=7.1 Hz, 2H), 4.06 (s, 1H), 3.93 (dd, $J_{1,2}$=6.5 Hz, $J_{1,3=9.6}$ Hz, 1H) 2.74 (dd, $J_{1,2}$=7.8 Hz, $J_{1,3}$=17.3 Hz, 1H), 2.35-2.33 (m, 2H), 2.03 (d, J=6.4 Hz, 1H), 1.26 (t, J=7.1 Hz, 3H), 0.86 (s,

9H), 0.14 (s, 3H), 0.07 (s, 3H); $^{13}$C NMR (CDCl$_3$, 100 MHz): δ 174.0, 128.4, 126.5, 74.8, 72.9, 60.6, 46.7, 28.3, 25.8, 18.1, 14.0, −4.2, −5.0; HR/MS (ESI) calculated for C$_{15}$H$_{28}$O$_4$SiNa [M+Na$^+$], 323.1655, found 323.1642.

The alcohol 11 (1 mmol) was dissolved at room temperature in dichloromethane (40 mL). Carbonyldiimidazole (1.46 g, 9.0 mmol) was added in one portion and the solution was stirred for 2 h. The solution was washed with a saturated solution of NH$_4$Cl (2×30 mL). The organic layer was dried over Na$_2$SO$_4$, filtered and concentrated. The residue was dissolved in pyridine (20 mL) at room temperature and NH$_2$OH.HCl (0.86 g, 12.0 mmol) was added in one portion. The solution was stirred for 4 h. Dichloromethane (50 mL) was then added and the resulting solution was washed with 10% solution of sulphuric acid (3×50 mL). The organic layer was dried over Na$_2$SO$_4$, filtered and concentrated. The N-hydroxycarbamate was purified by flash chromatography on silica gel (EtOAc/hexane=1:2) to give a white solid (1.87 g, 87%).

$^1$H NMR (CDCl$_3$, 400 MHz): δ 7.30 (s, 1H), 6.81 (s, 1H), 5.80 (d, J=10.1 Hz, 1H), 5.56 (d, J=10.1 Hz, 1H), 5.16-5.15 (m, 1H), 4.20-4.11 (m, 3H), 2.83-2.77 (m, 1H), 2.37-2.36 (m, 1H), 1.26 (t, J=7.1 Hz, 3H), 0.83 (s, 9H), 0.06 (s, 3H), 0.05 (s, 3H); $^{13}$C NMR (CDCl$_3$, 100 MHz): δ 173.3, 158.6, 129.0, 124.3, 71.0, 60.8, 46.9, 27.7, 25.6, 18.0, 14.0, −4.4, −5.2; HR/MS (ESI) calculated for C$_{16}$H$_{29}$NO$_6$SiNa [M+Na$^+$], 382.1662, found 323.1660.

To a solution of N-hydroxycarbamate (1.87 g, 5.2 mmol) in Et$_2$O (30 mL) at 0° C., was added p-toluenesulfonyl chloride (1.09 g, 5.7 mmol). Triethylamine (0.80 mL, 5.7 mmol) was then added slowly and the resulting white suspension was stirred for 12 h at room temperature. The mixture was washed with water and brine, and dried over Na$_2$SO$_4$. The solvent was removed under reduced pressure and the residue was purified by column chromatography on silica gel (EtOAc/hexane=1:4) to give the N-tosyloxycarbamate (3) (2.18 g, 82%) as a white solid.

$^1$H NMR (CDCl$_3$, 400 MHz): δ 8.03 (s, 1H), 7.87 (d, J=8.2 Hz, 2H), 7.34 (d, J=8.1 Hz, 2H) 5.70 (d, J=5 Hz, 1H), 5.18 (d, J=9.6 Hz, 1H), 5.01-4.99 (m, 1H), 4.17-4.08 (m, 2H), 4.01 (dd, J$_{1,2}$=7.1 Hz, J$_{1,3}$=10.3 Hz, 1H), 2.75-2.68 (m, 1H), 2.44 (s, 1H), 2.31-2.28 (m, 2H), 1.26 (t, J=7.1 Hz, 3H), 0.79 (s, 9H), 0.02 (s, 3H), −0.01 (s, 3H); $^{13}$C NMR (CDCl$_3$, 100 MHz): δ 173.1, 154.9, 146.1, 130.2, 129.7, 129.6, 128.9, 123.7, 78.9, 70.7, 60.8, 47.1, 28.0, 25.6, 21.8, 17.9, 14.0, −4.5, −5.2; HR/MS (ESI) calculated for C$_{23}$H$_{35}$NO$_8$SSiNa [M+Na$^+$], 536.1750, found 536.1740.

The N-tosyloxy carbamate (3) (1.14 g, 2.22 mmol), K$_2$CO$_3$ (1.53 g, 11.1 mmol) and (CuOTf)$_2$toluene (0.057 g, 0.111 mmol) were dissolved in acetonitrile (30 mL) at room temperature under nitrogen. The mixture was stirred vigorously for 12 h. The suspension was filtered through Celite and washed by CH$_2$Cl$_2$. The filtrate was concentrated. The crude product was dissolved in THF. To this solution trimethylsilyl azide (0.77 mL, 4.44 mmol) and TBAF (2.44 mL, 2.44 mmol) were added at 0° C. under nitrogen. The mixture was warmed to room temperature and stirred for 4 h. The mixture was filtered through silica gel and washed with EtOAc. The filtrate was evaporated and purified by column chromatography on silica gel (EtOAc/hexane=1:2) to give oxazolinidone (12) (0.7 g, 82%) as a light yellow oil.

$^1$H NMR (CDCl$_3$, 400 MHz): δ 6.02 (s, 1H), 4.44 (t, J=6.7 Hz, 1H), 4.25 (dd, J$_{1,2}$=6.7 Hz, J$_{1,3}$=8.7 Hz, 1H), 4.17 (q, J=7.1 Hz, 2H), 3.95-3.91 (m, 1H), 3.83-3.79 (m, 1H), 2.75 (dd, J$_{1,2}$=4.9 Hz, J$_{1,3}$=8.7 Hz, 1H), 2.19-2.12 (m, 1H), 1.97-1.90 (m, 1H), 1.27 (t, J=7.1 Hz, 3H), 0.85 (s, 9H), 0.15 (s, 3H), 0.07 (s, 3H); $^{13}$C NMR (CDCl$_3$, 100 MHz): δ 172.2, 158.7, 80.4, 71.0, 61.3, 58.1, 56.2, 43.2, 26.0, 25.6, 17.9, 14.0, −4.6, −5.4; HR/MS (ESI) calculated for C$_{16}$H$_{29}$N$_4$O$_5$Si [M+H$^+$], 385.1907, found 385.1904.

To a solution of oxazolinidone (12) in CH$_2$Cl$_2$ (15 mL), Boc$_2$O (0.41 mL, 1.76 mmol), Et$_3$N (0.33 mL, 2.34 mmol) and 4-dimethylaminopyridine (DMAP, 14.3 mg, 0.12 mmol) were sequentially added. The resulting mixture was stirred for 2 h at room temperature. The reaction mixture was washed with saturated NH$_4$Cl solution (2×20 mL). The organic layer was dried over Na$_2$SO$_4$, filtered, and concentrated. The crude solid was dissolved in dry THF. To the solution tetra-n-butylammonium fluoride (TBAF, 2.34 mL, 1 M in THF) was added at 0° C. The mixture was warmed to room temperature and stirred for 3 h. The solvent was removed under reduced pressure. The residue was purified by column chromatography on silica gel (EtOAc/hexane=1:2) to give oxazolinidone 13B (0.28 g, 69%) as a white solid.

$^1$H NMR (CDCl$_3$, 400 MHz): δ 6.86 (t, J=1.9 Hz, 1H), 5.09 (dd, J=3.9 Hz, J=7.2 Hz, 1H) 4.38 (t, J=7.3 Hz, 1H), 4.25 (q, J=7.1 Hz, 2H), 4.1 (dt, J=4.2 Hz, J=7.2 Hz, 1H) 2.79 (dd, J$_{1,2}$=4.1 Hz, J$_{1,3}$=18 Hz, 1H), 2.51 (dd, J$_{1,2}$=7.2 Hz, J$_{1,3}$=18 Hz, 1H), 1.55 (s, 9H), 1.31 (t, J=7.1 Hz, 3H), $^{13}$C NMR (CDCl$_3$, 100 MHz): δ 164.8, 150.9, 149.4, 132.7, 129.7, 85.0, 69.8, 61.6, 57.5, 56.1, 27.8, 26.1, 14.1; HR/MS (ESI) calculated for C$_{15}$H$_{20}$N$_4$O$_6$Na [M+Na$^+$], 375.1281, found 375.1279.

Cs$_2$CO$_3$ (31 mg, 0.094 mmol) was added to a solution of oxazolinidone 13B (0.33 g, 0.94 mmol) in ethanol. The mixture was stirred for 3 h at room temperature. Solvent was removed and the residue was purified by column chromatography on silica gel (EtOAc/hexane=1:4) to give azido carboxylate ester 19 (0.26 g, 83%) as a white solid.

$^1$H NMR (CDCl$_3$, 400 MHz): δ 6.87 (d, J=1.4 Hz, 1H), 5.14 (d, J=7.7 Hz, 1H), 4.47 (s, 1H), 4.21 (q, J=7.1 Hz, 2H), 3.79 (s, 2H), 2.91-2.81 (m, 2H), 2.35-2.29 (m, 1H), 1.46 (s, 9H), 1.30 (t, J=7.1 Hz, 3H), $^{13}$C NMR (CDCl$_3$, 100 MHz): δ 165.8, 155.9, 136.1, 130.5, 80.3, 65.1, 61.2, 56.8, 53.4, 29.6, 28.3, 14.1; HR/MS (ESI) calculated for C$_{14}$H$_{22}$N$_4$O$_5$Na [M+Na$^+$], 349.1488, found 349.1486.

DMP (0.54 g, 0.85 mmol) was added to a solution of azido carboxylate ester 19 (0.19 g, 0.57 mmol) in dry CH$_2$Cl$_2$ (10 mL). The mixture was stirred for 2 h at room temperature. Aqueous NaS$_2$O$_3$ and NaHCO$_3$ solution (30 mL, v/v=1:1) was added portionwise. The resulting solution was separated. The organic phase was washed with NaHCO$_3$ solution (20 mL) and brine (20 mL), dried over Na$_2$SO$_4$, concentrated. The crude product was dissolved in dry THF and added dropwise to a solution of LiAlH(OtBu)$_3$ (1 M in THF, 1.71 mL, 1.71 mmol) in THF (20 mL) at −20° C. The mixture was allowed to warm to room temperature and stirred 2 h. Saturated NH$_4$Cl solution was added to quench the reaction. The precipitate was removed by filtration through a celite pad. The filtrate was extracted with CH$_2$Cl$_2$ three times, and the combined organic layer was washed with brine and dried over Na$_2$SO$_4$. The solvent was removed under reduced pressure, and the residue was purified by column chromatography on silica gel (EtOAc/hexane=1:1) to give azido carboxylate ester 2B (0.145 g, 78%) as a white solid.

$^1$H NMR (CDCl$_3$, 400 MHz): δ 6.81 (t, 1H), 5.08 (d, J=4.8 Hz, 1H), 4.54 (s, 1H), 4.39 (s, 1H), 4.21 (q, J=7.1 Hz, 2H), 3.67-3.61 (m, 1H), 3.46-3.40 (m, 1H), 2.92 (dd, J=5.2 Hz, J=17.5 Hz, 1H), 2.44-2.36 (m, 1H), 1.46 (s, 9H), 1.29 (t, J=7.1 Hz, 3H), $^{13}$C NMR (CDCl$_3$, 100 MHz): δ 165.7, 157.1, 138.5, 127.6, 81.1, 71.4, 61.1, 58.1, 57.9, 29.6, 28.2, 14.1; BRIMS (ESI) calculated for C$_{14}$H$_{22}$N$_4$O$_5$Na [M+Na$^+$], 349.1488, found 349.1492.

To a solution of PPh$_3$ (0.204 g, 0.78 mmol) and azido carboxylate ester 2B (0.101 mg, 0.31 mmol) in THF (10 mL), DEAD (0.123 mL, 0.78 mmol) in THF (1 mL) was added and the resulting mixture was stirred at 0° C. After 3 h, mixture was concentrated, and purified by column chromatography on silica gel (EtOAc/hexane=1:7) to give azabicyclo carboxylate ester 16 (0.079 g, 83%) as colorless oil.

IR (neat) $v_{max}$=3420, 3019, 2982, 2110, 1701, 1260, 1215, 1153, 756 cm$^{-1}$; $^1$H NMR (CDCl$_3$, 400 MHz): δ 7.19 (dd, $J_{1,2}$=3.3 Hz, $J_{1,3}$=4.6 Hz, 1H), 4.32-4.30 (m, 1H), 4.21 (dq, J=2.1 Hz, J=7.1 Hz, 2H), 3.13-3.05 (m, 2H), 2.91 (dt, J=2.0 Hz, J=17.5 Hz, 1H) 2.37 (ddd, J=3.2 Hz, J=5.4 Hz, J=17.5 Hz, 1H), 1.46 (s, 9H), 1.29 (t, J=7.1 Hz, 3H), $^{13}$C NMR (CDCl$_3$, 100 MHz): δ 165.5, 160.5, 133.3, 129.7, 82.5, 61.0, 52.7, 40.6, 33.3, 27.8, 25.9, 14.2; HR/MS (ESI) calculated for C$_{14}$H$_{20}$N$_4$O$_4$Na [M+Na$^+$], 331.1382, found 331.1369.

To a solution of azabicyclo carboxylate ester 16 (55 mg, 0.18 mmol) in 3-pentanol (2.5 mL), BF$_3$.OEt$_2$ (0.5 Min 3-pentanol, 0.72 mL, 0.36 mmol) was added dropwise, and the resulting mixture was stirred at −20° C. After 2 h, saturated aqueous NaHCO$_3$ was added to quench the reaction. The product was extracted with CH$_2$Cl$_2$ (3×20 mL) and the combined organic layer was dried over Na$_2$SO$_4$. The solvent was removed under reduced pressure, and the residue was purified by column chromatography (EtOAc/hexane=1:6) to give azido carboxylate ester 14A (57 mg, 80%) as a white solid.

$^1$H NMR (CDCl$_3$, 400 MHz): δ 6.77 (s, 1H), 4.92 (d, J=5.2 Hz, 1H), 4.49 (d, J=4.3 Hz, 1H), 4.22 (dq, J=1.0 Hz, J=5.7 Hz, 2H), 3.34 (t, J=4.4 Hz, 1H), 3.12-3.10 (m, 1H), 2.91 (dd, $J_{1,2}$=5.8 Hz, $J_{1,3}$=14.1 Hz, 1H) 2.22-2.16 (m, 1H), 1.53-1.50 (m, 4H), 1.45 (s, 9H), 1.29 (t, J=5.7 Hz, 3H), 0.91 (t, J=5.9 Hz, 3H), HR/MS (ESI) calculated for C$_{19}$H$_{32}$N$_4$O$_5$Na [M+Na$^+$], 419.2270, found 419.2267.

A mixture of azido carboxylate ester 14A (29 mg, 0.073) and TFA (0.11 mL, 1.46 mmol) in CH$_2$Cl$_2$ (0.5 mL) was stirred for 2 h at room temperature and then washed by saturated NaHCO$_3$ solution. The organic phase was dried over Na$_2$SO$_4$, filtered and concentrated. The residue was dissolved in dry CH$_2$Cl$_2$. Acetic anhydride (0.011 mL, 0.11 mmol) and Et$_3$N (0.03 mL, 0.22 mmol) were added. The mixture was stirred for 3 h at room temperature and then washed by NH$_4$Cl solution. The organic phase was dried over Na$_2$SO$_4$, filtered and concentrated. The residue was purified by column chromatography (EtOAc/hexane=1:1) on silica gel to give azido carboxylate ester 14B (21 mg, 84%) as a white solid.

$^1$H NMR (CDCl$_3$, 400 MHz): δ 6.77 (s, 1H), 6.03 (d, J=7.4 Hz, 1H), 4.54 (d, J=8.7 Hz, 1H), 4.28-4.17 (m, 3H), 3.37-3.31 (m, 2H), 2.91 (dd, $J_{1,2}$=5.6 Hz, $J_{1,3}$=17.6 Hz, 1H) 2.26-2.17 (m, 1H), 2.02 (s, 1H), 1.53-1.45 (m, 4H), 1.28 (t, J=7.1 Hz, 3H), 0.91-0.86 (dt, J=4.2 Hz, J=7.4 Hz, 3H), $^{13}$C NMR (CDCl$_3$, 100 MHz): δ 171.1, 165.8, 137.9, 128.1, 82.0, 73.4, 61.0, 57.9, 57.2, 30.5, 26.2, 25.6, 23.5, 14.1, 9.5, 9.2; HR/MS (ESI) calculated for C$_{16}$H$_{26}$N$_4$O$_4$Na [M+Na$^+$], 361.1852, found 361.1843.

PPh$_3$ was added to a solution of azide 14B (23 mg, 0.068 mmol) in THF/water (0.25 mL, 4:1 v/v) at room temperature. The mixture was refluxed for 3 h. The reaction mixture was cooled to room temperature. The solvent was removed under reduced pressure. The residue was diluted with CH$_2$Cl$_2$ and washed with brine (10 mL). The organic layer was dried over Na$_2$SO$_4$, filtered and concentrated. The residue was purified by column chromatography (CH$_2$Cl$_2$/MeOH=5:1) on silica gel to give amine 1 (19 mg, 90%) as colorless oil.

$^1$H NMR (CDCl$_3$, 400 MHz): δ 6.76 (s, 1H), 5.95 (d, J=8.0 Hz, 1H), 4.18 (q, J=6.8 Hz, 3H), 3.52 (dd, J=8.6 Hz, J=18.4 Hz, 1H), 3.34-3.29 (m, 1H), 3.19 (dt, $J_{1,2}$=5.4 Hz, $J_{1,3}$=10.0 Hz, 1H), 2.73 (dd, $J_{1,2}$=5.0 Hz, $J_{1,3}$=17.7 Hz, 1H) 2.16-2.09 (m, 1H), 2.02 (s, 1H), 1.51-1.46 (m, 4H), 1.26 (t, J=7.1 Hz, 3H), 0.90-0.85 (m, 6H), $^{13}$C NMR (CDCl$_3$, 100 MHz): δ 171.0, 166.3, 137.6, 129.4, 81.6, 74.8, 60.8, 58.8, 49.1, 33.5, 26.2, 25.6, 23.6, 14.1, 9.5, 9.3; HR/MS (ESI) calculated for C$_{16}$H$_{29}$N$_2$O$_4$. [M+H$^+$], 313.2127, found 313.2126.

A solution of amine 1 (19 mg, 0.061 mmol) in ethanol (1 mL) was added slowly to a hot (60° C.) solution of phosphoric acid (85%, 11.5 mg, 0.061 mmol) in ethanol (0.2 mL). The resulting mixture was stirred for 3 h. After cooling to 0° C., the precipitates were collected by filtration and rinsed with cold acetone (2×5 mL) to give tamiflu as a white crystal (21 mg, 85%).

$^1$H NMR (CDCl$_3$, 400 MHz): δ 6.86 (s, 1H), 4.34 (d, J=8.9 Hz, 1H), 4.25 (dq, J=1.5 Hz, J=7.2 Hz, 2H), 4.07 (dd, J=9.0 Hz, J=11.7 Hz, 1H), 3.74 (t, J=6.5 Hz, 1H), 3.63-3.54 (m, 1H), 2.97 (dd, $J_{1,2}$=5.4 Hz, $J_{1,3}$=17.3 Hz, 1H) 2.56-2.49 (m, 1H), 2.01 (s, 1H), 1.58-1.47 (m, 4H), 1.29 (t, J=7.1 Hz, 3H), 0.87 (dt, $J_{1,2}$=7.4 Hz, $J_{1,4}$=17.6 Hz, 6H), $^{13}$C NMR (D$_2$O, 100 MHz): δ 175.2, 167.4, 137.8, 127.6, 84.3, 75.1, 62.4, 52.6, 49.1, 28.1, 25.4, 25.0, 22.3, 13.3, 8.5, 8.4; $^{31}$P NMR (162 MHz, D$_2$O) δ 0.65; HR/MS (ESI) calculated for C$_{16}$H$_{29}$N$_2$O$_4$ [M+H$^+$], 313.2127, found 313.2122.

Figure 10:
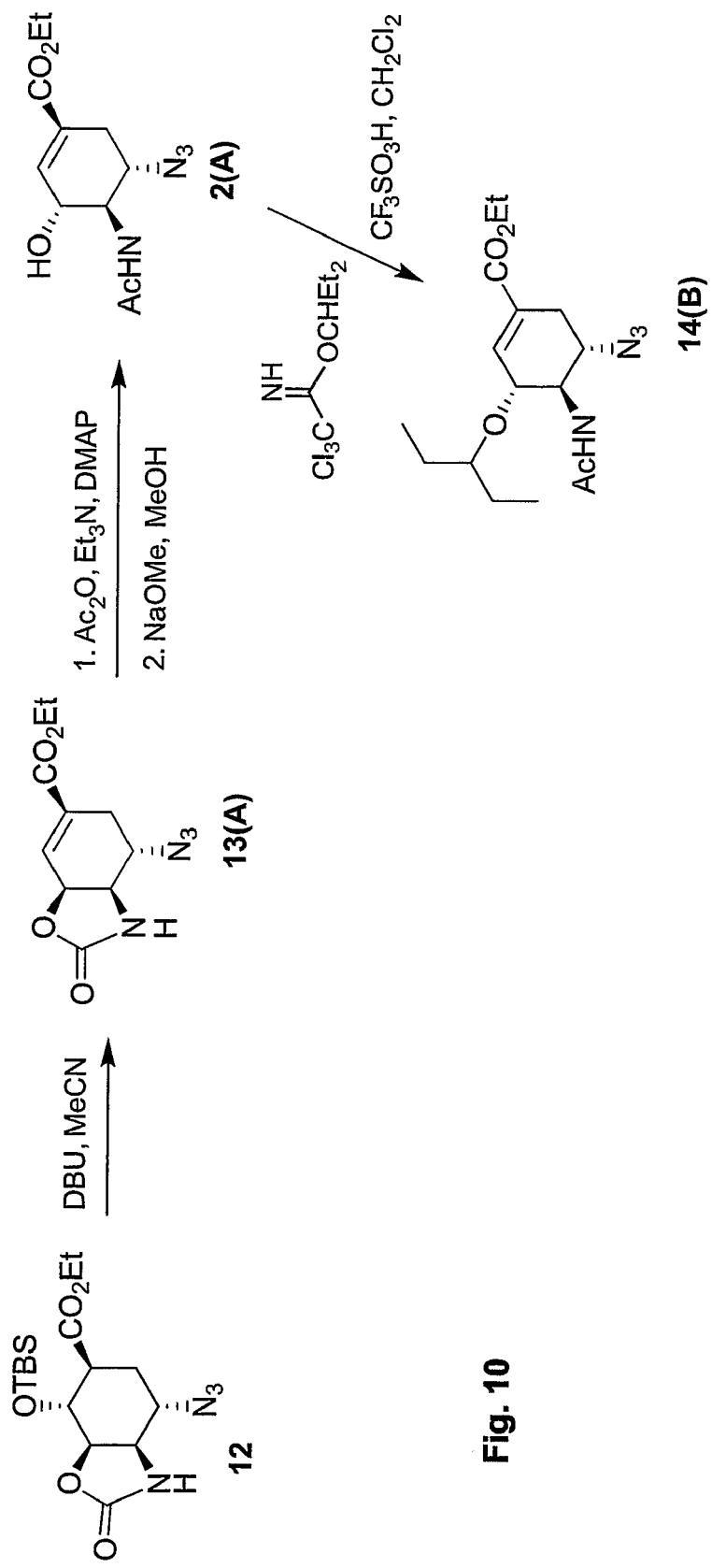
FIG. 10 depicts a further embodiment (cf. also FIG. 8) of the last steps of the synthesis of Oseltamivir Phosphate (1.$H_3PO_4$).

Proceeding according to an alternative synthesis route (cf. e.g. FIG. 2 and FIG. 10), Oxazolinidone (12) (1 mmol) was dissolved in anhydrous CH$_3$CN (5 mL). The mixture was stirred overnight at room temperature in the presence of DBU (2 mmol). It was then diluted with CH$_2$Cl$_2$ (20 mL) and washed with brine (2×20 mL). The organic layer was dried over Na$_2$SO$_4$, filtered and evaporated under reduced pressure. Oxazolinidone (13A) was purified by flashing column chromatography.

To a stirring solution of oxazolinidone (13A) (1 mmol) in acetonitrile (30 mL) under argon, Et$_3$N (2 mmol), acetic anhydride (1 mmol), and 4-dimethylaminopyridine (DMAP, 2 mmol) were sequentially added. The resulting mixture was warmed to 70° C. and further portions of Et$_3$N (6 mmol), acetic anhydride (3 mmol), and DMAP (6 mmol) were added. After 24 h, the reaction mixture was quenched with saturated NH$_4$Cl solution, diluted with distilled water and extracted with CH$_2$Cl$_2$ (3×20 mL). The combined organic layers were dried over Na$_2$SO$_4$, filtered, and concentrated. After flash chromatographic purification (EtOAc/hexane) pure acetylated lactam was obtained and dissolved in methanol (20 mL). To which was added sodium methoxide (0.3 mmol) at room temperature. The mixture was stirred at room temperature for 30 min followed by treatment with Amberlyst 15 ion-exchange resin for 5 min. The mixture was diluted with methanol and filtered through Celite and silica gel. The filter pad was rinsed with methanol after filtration. The combined filtrates were concentrated under reduced pressure to afford azido carboxylate ester (2A) without further purification.

A solution of 3-pentanol (1 mmol) in anhydrous Et$_2$O (0.2 mL) was added dropwise to NaH (0.1 mmol; 60% in mineral oil) suspended in Et$_2$O (1 mL) under nitrogen. The mixture was stirred for 10 min at room temperature and then added dropwise over a period of 20 min to a solution of trichloroacetonitrile (1.5 mmol) in Et$_2$O (1 mL) at −5° C. under nitrogen. The reaction mixture was warmed to room temperature, and stirred for 2 h. After removal of solvent, the residue was triturated with MeOH/hexane with vigorous stirring to give precipitates, which were filtered off and washed with cold hexane. The filtrate was evaporated under reduced pressure to give 3-pentyl trichloroacetimidate. The freshly prepared 3-pentyl trichloroacetimidate (0.75 mmol) and CF$_3$SO$_3$H (0.075 mmol) were added to a solution of azido carboxylate ester (2A) (0.6 mmol) in CH$_2$Cl$_2$ (5 mL) under nitrogen. The reaction mixture was stirred at room temperature for 24 h, during which more imidate and CF$_3$SO$_3$H (0.075 mmol) were added 5 times every 4 h period. The reaction was quenched with 5% aqueous NaHCO$_3$ solution. The aqueous layer was extracted with CH$_2$Cl$_2$ (2×). The combined organic phase was washed with brine, dried over Na$_2$SO$_4$ and concentrated in vacuo. The residue was purified by flash column chromatography (EtOAc/hexane) to afford the product (14B). Azide (14B) can then be converted to amine (1) as described above.

The listing or discussion of a previously published document in this specification should not necessarily be taken as an acknowledgement that the document is part of the state of the art or is common general knowledge.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

One skilled in the art would readily appreciate that the present invention is well adapted to carry out the objects and obtain the ends and advantages mentioned, as well as those inherent therein. Further, it will be readily apparent to one skilled in the art that varying substitutions and modifications may be made to the invention disclosed herein without departing from the scope and spirit of the invention. The molecular complexes and the methods, procedures, treatments, molecules, specific compounds described herein are presently representative of preferred embodiments are exemplary and are not intended as limitations on the scope of the invention. Changes therein and other uses will occur to those skilled in the art which are encompassed within the spirit of the invention are defined by the scope of the claims.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" etc. shall be read expansively and without limitation, and are not limited to only the listed components they directly reference, but include also other non-specified components or elements. As such they may be exchanged with each other. Additionally, the terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed.

Other embodiments are within the following claims. In addition, where features or aspects of the invention are described in terms of Markush groups, those skilled in the art will recognize that the invention is also thereby described in terms of any individual member or subgroup of members of the Markush group.

What is claimed is:

1. A process of forming a 4,5-diamino cyclohexene carboxylate ester of general formula (1)

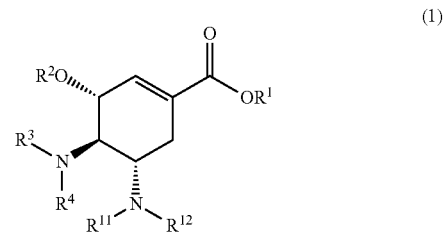

or a pharmaceutically acceptable salt thereof, wherein $R^1$-$R^3$ are independently selected from the group consisting of a silyl-group, an aliphatic group, an alicyclic group, an aromatic group, an arylaliphatic group, and an arylalicyclic group, comprising 0 to about 3 heteroatoms selected from the group N, O, S, Se and Si, wherein $R^4$, $R^{11}$ and $R^{12}$ are independently selected from the group consisting of H, a silyl-group, and an aliphatic, alicyclic, aromatic, arylaliphatic, and arylalicyclic group, comprising 0 to about 3 heteroatoms selected from the group N, O, S, Se and Si, the process comprising:

(a) reacting a 3,4-dihydropyran compound (9)

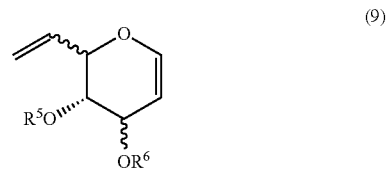

wherein $R^5$ and $R^6$ are independently selected suitable protecting groups, and wherein the symbols ∿ indicates that the bond may have any configuration, to form an aldehyde of general formula (4)

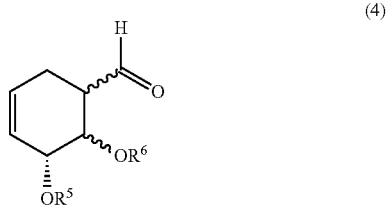

(b) oxidizing aldehyde (4) to carboxylic acid ester (10)

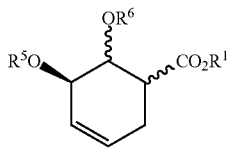
(10)

(c) replacing protecting group $R^5$ of carboxylic acid ester (10) by an N-substituted carbamoyl group, thereby forming N-substituted carbamate (3)

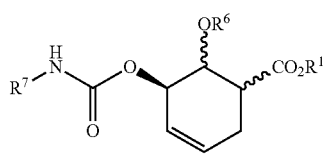
(3)

wherein $R^7$ is a suitable protecting group, (d) reacting N-substituted carbamate (3) to form oxazolinidone (12)

(12)

(e) removing moiety $OR^6$ from oxazolinidone (12) to form oxazolinidone (13)

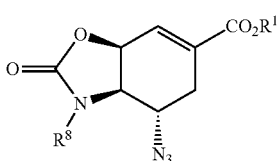
(13)

wherein $R^8$ is H or one of a silyl-group, an aliphatic group, an alicyclic group, an aromatic group, an arylaliphatic group, and an arylalicyclic group, comprising 0 to about 3 heteroatoms selected from the group N, O, S, Se and Si, (f) reacting oxazolinidone (13) to form azido carboxylate ester (2)

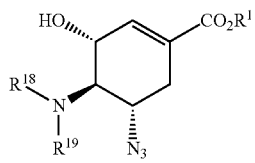
(2)

wherein $R^{18}$ and $R^{19}$ are independently selected from the group consisting of a silyl-group, an aliphatic, alicyclic, aromatic, arylaliphatic, and arylalicyclic group, comprising 0 to about 3 heteroatoms selected from the group N, O, S, Se and Si, and (g) converting azido carboxylate ester (2) to 4,5-diamino cyclohexene carboxylate ester (1).

2. The process of claim 1, further comprising forming a pharmaceutically acceptable salt of 4,5-diamino cyclohexene carboxylate ester (1).

3. The process of claim 1, wherein in compounds (4), (9) and (10) $R^5$, and in compounds (3), (4), (9), (10) and (12) $R^6$ are independently selected from the group consisting of a silyl-group, an aliphatic, alicyclic, aromatic, arylaliphatic, and arylalicyclic group, comprising 0 to about 3 heteroatoms selected from the group N, O, S, Se and Si.

4. The process of claim 1, wherein in compound (1) $R^3$ and in compound (2) $R^{18}$ are an independently selected acyl group.

5. The process of claim 1, wherein in compounds (4), (9) and (10) $R^5$, in compounds (3), (4), (9), (10) and (12) $R^6$, and in N-substituted carbamate (3) $R^7$, are independently selected from the group consisting of methyl-, ethyl-, n-propyl, isopropyl-, acetyl-, benzyl-, benzoyl-, p-methoxy-benzyl-, 2,6-dimethoxybenzyl-, tosyl-, tetrahydropyranyl-, methoxymethyl-, β-methoxyethoxymethyl-, triphenylmethyl-, allyl-, 1,1,1,3,3,3-hexafluoroisopropyl-, trimethylsilyl-, triethylsilyl-, tri-isopropyl-silyl-, di-isopropyl-methyl-silyl-, tertiary-butyl-dimethyl-silyl-, tertiary-butyl-diphenyl-silyl-, (tris(trimethylsilyl)silyl)-, trifluorosulfonyl-, toluenesulfonyl-, p-methoxybenzyl-, tertiary-butyl-, methylsulfonyl-, allylsulfonyl-, allyl-, allylsilyl-, pivaloyl-, methylthiomethyl- and 2-(dimethyl(2-naphthylmethyl)silyl)ethoxycarbanoyl.

6. The process of claim 1, wherein in compounds (4), (9) and (10) $R^5$ consists of a methylene linker and a moiety $R^{10}$, the methylene linker connecting moiety $R^{10}$ to the 4-hydroxy group of 3,4-dihydropyran compound (9), wherein $R^{10}$ is one of an aliphatic, alicyclic, aromatic, arylaliphatic, and an arylalicyclic group, comprising 0 to about 3 heteroatoms selected from the group N, O, S, Se and Si, such that 3,4-dihydropyran compound (9) can be represented by formula (9A)

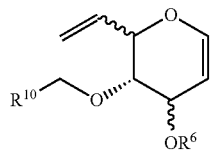
(9A)

and wherein the 3,4-dihydropyran compound (9A) is obtained by:

(i) reacting acetal (7)

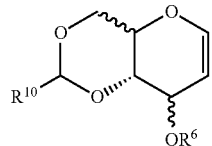
(7)

to form 3,4-dihydropyran compound (8)

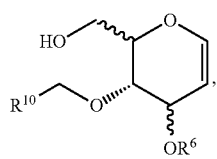
(8)

and (ii) removing the hydroxy group of 3,4-dihydropyran compound (8) to form 3,4-dihydropyran compound (9A).

7. The process of claim 6, wherein the acetal (7) is obtained by:

(i) reacting 3,4-dihydropyran compound (5)

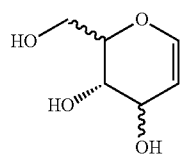
(5)

to form acetal (6)

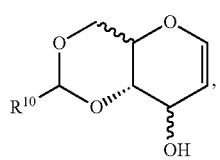
(6)

and (ii) shielding the 3-hydroxy group of acetal (6) by forming acetal (7) therefrom.

8. The process of claim 1, wherein converting azido carboxylate ester (2) to 4,5-diamino cyclohexene carboxylate ester (1) comprises:

(i) reacting azido carboxylate ester (2) to form azido carboxylate ester (14)

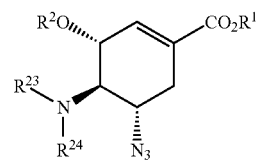
(14)

and (ii) converting azido carboxylate ester (14) to 4,5-diamino cyclohexene carboxylate ester (1), wherein $R^{23}$ and $R^{24}$ are independent from one another H, a silyl-group, an aliphatic group, an alicyclic group, an aromatic group, an arylaliphatic group or an arylalicyclic group.

9. The process of claim 1, wherein reacting 3,4-dihydropyran compound (9) to form an aldehyde (4) comprises exposing 3,4-dihydropyran compound (9) to an elevated temperature.

10. The process of claim 1, wherein oxidizing aldehyde (4) to carboxylic acid ester (10) comprises contacting aldehyde (4) with an oxidizing agent.

11. The process of claim 1, wherein oxidizing aldehyde (4) to carboxylic acid ester (10) comprises forming a carboxylic acid (10A):

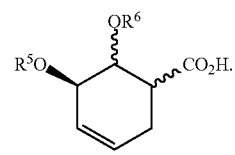
(10A)

12. The process of claim 1, wherein replacing protecting group $R^5$ of carboxylic acid ester (10) by an N-substituted carbamoyl group comprises converting carboxylic acid ester (10) to hydroxy carboxylic acid ester (11)

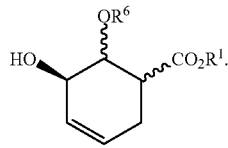
(11)

13. The process of claim 12, wherein $R^5$ is p-methoxybenzyl-, and wherein converting carboxylic acid ester (10) to hydroxy carboxylic acid ester (11) comprises removing moiety $R^5$ by contacting carboxylic acid ester (10) with one of ceric ammonium nitrate, 2,3,-dichloro-5,6-dicyano-1,4-benzoquinone (DDQ), $CBr_4$ in methanol, and $NaBH_3(CN)$/ $BF_3.Et_2O$.

14. The process of claim 12, wherein hydroxy carboxylic acid ester (11) is converted to N-substituted carbamate (3), the conversion comprising contacting hydroxy carboxylic acid ester (11) with 1,1'-carbonyldiimidazole (CDI), thereby forming carbamate (3A)

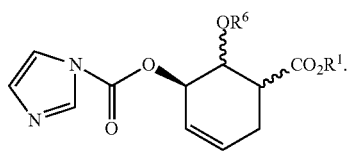

(3A)

15. The process of claim 14, wherein carbamate (3A) is further reacted with a compound (15) of general formula $R^7$—X, wherein X is a group selected from halogen, a cyano, an isocyano and a thiocyano group, thereby forming N-substituted carbamate (3).

16. The process of claim 1, wherein reacting N-substituted carbamate (3) to form oxazolinidone (12) comprises contacting N-substituted carbamate (3) with a metal carbonate in the presence of a suitable catalyst.

17. The process of claim 16, wherein reacting N-substituted carbamate (3) to form oxazolinidone (12) further comprises adding an azido compound under suitable conditions.

18. The process of claim 1, wherein removing moiety $OR^6$ from oxazolinidone (12) to form oxazolinidone (13) comprises contacting oxazolinidone (12) with a Bronsted base.

19. The process of claim 1, wherein reacting oxazolinidone (13) to form azido carboxylate ester (2) comprises contacting oxazolinidone (13) with a molecule of general formula $R^3$-A-$R^3$ under suitable conditions, $R^3$ being one of a silyl-group, an aliphatic group, an alicyclic group, an aromatic group, an arylaliphatic group, and an arylalicyclic group comprising 0 to about 3 heteroatoms selected from the group N, O, S, Se and Si wherein A is one of O, S, Se, N and P.

20. The process of claim 1, wherein reacting oxazolinidone (2) to form 4,5-diamino cyclohexene carboxylate ester (1) comprises forming an azabicyclo carboxylate ester of the formula (16)

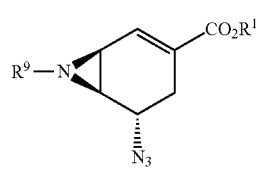

(16)

wherein $R^9$ is selected from the group consisting of a silyl-group, an aliphatic, an alicyclic, an aromatic, an arylaliphatic, and an arylalicyclic group.

21. The process of claim 20, wherein azabicyclo carboxylate ester (16) is reacted to form azido carboxylate ester (14).

* * * * *